(12) United States Patent
Fiedotin et al.

(10) Patent No.: US 8,290,787 B2
(45) Date of Patent: *Oct. 16, 2012

(54) METHOD FOR GENERATING AND TRANSMITTING PRESCRIPTION RENEWAL REQUEST INFORMATION

(75) Inventors: Richard Alan Fiedotin, San Mateo, CA (US); Geoffrey David Hyde, San Francisco, CA (US); Diane Elizabeth Fraser, Palo Alto, CA (US)

(73) Assignee: Epocrates, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/010,668

(22) Filed: Jan. 20, 2011

(65) Prior Publication Data

US 2011/0119091 A1    May 19, 2011

Related U.S. Application Data

(63) Continuation of application No. 10/167,803, filed on Jun. 11, 2002, now Pat. No. 7,890,350.

(51) Int. Cl.
*G06Q 50/00* (2012.01)
(52) U.S. Cl. .................... 705/2; 705/3; 600/300
(58) Field of Classification Search .......... None
See application file for complete search history.

(56) References Cited

U.S. PATENT DOCUMENTS

| | | | |
|---|---|---|---|
| 4,847,764 A | 7/1989 | Halvorson | 364/413.02 |
| 5,737,539 A * | 4/1998 | Edelson et al. | 705/3 |
| 5,758,095 A | 5/1998 | Albaum et al. | 395/202 |
| 5,772,585 A | 6/1998 | Lavin et al. | 600/300 |
| 5,845,255 A | 12/1998 | Mayaud | 705/3 |
| 5,950,632 A | 9/1999 | Reber et al. | 128/898 |
| 6,021,392 A | 2/2000 | Lester et al. | 705/2 |
| 6,076,166 A | 6/2000 | Moshfeghi et al. | 713/201 |
| 6,198,383 B1 | 3/2001 | Sekura et al. | 340/309.4 |

(Continued)

FOREIGN PATENT DOCUMENTS

JP    10508131    8/1998

OTHER PUBLICATIONS

Supplementary European Search Report for EP 03757496 dated Mar. 1, 2010, 2 pgs.

(Continued)

*Primary Examiner* — David Rines
(74) *Attorney, Agent, or Firm* — Morgan, Lewis & Bockius LLP

(57) ABSTRACT

A method for providing prescription renewal request information via an electronic network. Upon receiving a request from a client for renewal request information for a particular prescriber, a report is generated containing the requested renewal request information and transmitted to the client. The transmitted report allows the client to easily review renewal request information and helps the client to manage appointments with patients whom the prescriber wishes to see. Depending on the client request, the transmitted report may be an "active renewals" page containing renewal request information regarding renewal requests that the prescriber has not reviewed, an "archived renewals" page containing renewed request information regarding renewal requests that the prescriber has reviewed, an "appointment" page containing renewal request information regarding patients with whom the prescriber wishes to make an appointment, or a "prescription detail" page containing detailed renewal request information regarding a particular renewal request.

33 Claims, 17 Drawing Sheets

U.S. PATENT DOCUMENTS

| | | | |
|---|---|---|---|
| 6,283,761 B1 | 9/2001 | Joao | 434/236 |
| 6,347,329 B1 | 2/2002 | Evans | 709/202 |
| 6,347,705 B1 | 2/2002 | Futrell | 206/534 |
| 6,381,583 B1 | 4/2002 | Kenney | 705/26 |
| 6,493,427 B1 | 12/2002 | Kobylevsky et al. | 379/67.1 |
| 6,757,898 B1 | 6/2004 | Ilsen et al. | 718/203 |
| 6,842,736 B1 | 1/2005 | Brzozowski | 705/2 |
| 6,973,435 B1 | 12/2005 | Sioufi et al. | 705/2 |
| 7,286,996 B1 | 10/2007 | Fiedotin et al. | 705/2 |
| 2001/0032099 A1 | 10/2001 | Joao | 705/2 |
| 2001/0037218 A1 | 11/2001 | Kaker et al. | 705/2 |
| 2002/0029223 A1 | 3/2002 | Rice et al. | 707/104.1 |
| 2002/0042725 A1 | 4/2002 | Mayaud | 705/2 |
| 2002/0042726 A1 | 4/2002 | Mayaud | 705/2 |
| 2002/0062175 A1 | 5/2002 | Lion | 700/237 |
| 2003/0050799 A1 | 3/2003 | Jay et al. | 705/2 |
| 2003/0074234 A1 | 4/2003 | Stasny | 705/4 |
| 2003/0130868 A1 | 7/2003 | Coelho | 705/2 |
| 2003/0130875 A1* | 7/2003 | Hawash et al. | 705/3 |
| 2003/0154106 A1 | 8/2003 | Marks | 705/2 |
| 2005/0065818 A1 | 3/2005 | Brinkman et al. | 705/2 |

OTHER PUBLICATIONS

International Search Report for PCT/US03/18574 dated Aug. 14, 2003, 5 pgs.

European Office Action for 03757496.9 dated Mar. 22, 2011, 6 pgs.

* cited by examiner

FIG. 3

- 320 — Prescriber Memory
- 322 — Operating System
- 324 — Remote Access Procedures
- 326 — Renewal Authorization Procedure
- 328 — Renewal Database
- 330(1) — Patient Profile 1
- 332 — Patient Information
- 334(1) — Prescription Profile 1
- 336 — Prescribed Pharmaceutical
- 338 — Prescriber
- 340 — Dosage
- 342 — Refill Details
- 344 — Other Prescription Details
- 334(N) — Prescription Profile N
- 330(N) — Patient Profile N
- 350 — Formulary Database
- 352 — Drug-Drug Reaction Database

FIG. 2

- 120 — Dispenser Memory
- 122 — Operating System
- 124 — Remote Access Procedures
- 126 — Prescription Filling procedure
- 128 — Dispenser database
- 130(1) — Prescription 1
- 132 — Patient Information
- 134 — Drug ID / Name
- 136 — Dosage
- 138 — Prescribing Physician
- 140 — Refill Details
- 142 — Renewal Details
- 130(N) — Prescription N
- 146 — Formulary Database
- 148 — Drug-Drug Reaction Database

Active Renewal Requests

| | Prescription No. | Patient Name | DOB | Medication | Request Date | Printed |
|---|---|---|---|---|---|---|
| ☐ | 001829230 | Doe, John | 10/23/43 | Lipitor | 11/01/00 | ✓ |
| ☑ | 001675821 | Smith, Pam | 03/04/45 | Levoxyl | 11/01/00 | |
| ☐ | 001832100 | Nelson, Tim | 01/17/32 | Glucophage | 11/03/00 | |
| ☑ | 001768402 | Roberts, Norma | 06/30/54 | Nadolol | 10/31/00 | ✓ |

[Print List] [Print Selected] [Print All]

[Active Renewals] [Archived Renewals] [Appointment Tickler] [Home]

FIG. 11A

Archived Renewal Requests

Home ~1244

Filter By

Last Name | First Name | Medication | Approval Date Range | Status
--- | --- | --- | --- | ---
 | | | to | }1234

Update View | Reset ~1232

1230

| | Prescription No. | Patient Name | DOB | Medication | Approval Date | Status | Printed |
|---|---|---|---|---|---|---|---|
| ☐ | 001829230 ~1202 | Doe, John ~1204 | 10/23/43 ~1206 | Lipitor ~1208 | 11/01/00 ~1210 | Y ~1212 | ✓ ~1214 |
| ☑ | 001675821 | Smith, Pam | 03/04/45 | Levoxyl | 11/01/00 | N | |
| ☐ | 001832100 | Nelson, Tim | 01/17/32 | Glucophage | 11/03/00 | Y | |
| ☐ | 001768402 | Roberts, Norma | 06/30/54 | Nadolol | 10/31/00 | E | ✓ |

1226

Print List ~1220    Print Selected ~1222    Print All ~1224

Active Renewals ~1240
Archived Renewals ~1242
Appointment Tickler

FIG. 11B

Appointment Tickler

[Home] 1294

[Update List] 1280

| | Prescription No. | Patient Name | DOB | Medication | Approval Date | Status | Patient Phone | Made Appt. |
|---|---|---|---|---|---|---|---|---|
| ☐ | 001829230 | Doe, John | 10/23/43 | Lipitor | 11/01/00 | Y | 401-555-2031 | ☐ |
| ☐ | 001675821 | Smith, Pam | 03/04/45 | Levoxyl | 11/01/00 | N | 401-555-9504 | ☑ |
| ☑ | 001832100 | Nelson, Tim | 01/17/32 | Glucophage | 11/03/00 | Y | 401-555-4850 | ☐ |
| ☐ | 001768402 | Roberts, Norma | 06/30/54 | Nadolol | 10/31/00 | E | 401-555-7887 | ☐ |

[Print List] [Print Selected] [Print All]

[Active Renewals]
[Archived Renewals]
[Appointment Tickler]

FIG. 11C

Prescription Details

Smith, Pam — 1306
Sex: F    DOB: 03/04/45
Rx Source: Advance PCS
Rx Identifier: 001675821

Claritin

Sig: TAKE 1 BY MOUTH 2 TIMES DAILY — 1316
Disp: 60    Refills: 3
Request Date:    11/01/00
Last Refill:    10/15/00
Date Signed:    Pending
☐ Must make an appointment.

[Print]  [Close]

FIG. 11D

METHOD FOR GENERATING AND TRANSMITTING PRESCRIPTION RENEWAL REQUEST INFORMATION

CROSS REFERENCE TO RELATED APPLICATIONS

This application is a continuation of U.S. patent application Ser. No. 10/167,803, filed Jun. 11, 2002 now U.S. Pat. No. 7,890,350, which is hereby incorporated by reference in its entirety.

TECHNICAL FIELD

The present invention relates generally to the pharmaceutical prescription industry. More particularly, the invention is directed to generating and transmitting prescription renewal request information.

BACKGROUND

A physician-patient meeting usually results in a diagnosis, with the physician writing a prescription for a pharmaceutical drug to treat the patient's diagnosed problem. In writing the prescription, the physician will ideally verify that the pharmaceutical drug is on formulary. The formulary is a list that informs prescribing physicians and pharmacists of the pharmaceuticals for which insurance providers will pay. The formulary may contain brand name or generic pharmaceuticals or both. In this regard, generic pharmaceuticals have the same active ingredients, strength, and dosage as their brand name counterparts, and are therapeutically equivalent to them.

In situations where patients have a chronic condition, such as high blood pressure or high cholesterol, the patient requires medication for a sustained period. An original prescription for a pharmaceutical drug to treat a chronic condition (a chronic medication), may include one or more refills authorizing the pharmacy to dispense additional medication in accordance with the original prescription without further authorization from the prescribing physician. Moreover, patients with chronic conditions often require the physician to re-prescribe or renew prescriptions for chronic medication over time. Before renewing a prescription, however, the physician may wish to make an appointment with the patient to re-evaluate or re-diagnose the patient's medical situation. The original prescription typically contains the patient's name, the pharmaceutical's name, the prescribed dosage, and any renewal or refill information.

The original prescription is typically given to a pharmacy (whether retail, mail-order, on-line, or otherwise) that inputs the prescription information, along with the patient's pharmacy benefits and insurance information, into a computer and checks with the appropriate Pharmacy Benefit Management organization (PBM), or a PBM group at an insurance company, via telephone or on-line computer connection to ensure that the prescribed pharmaceutical drug is on the formulary.

PBMs track the prescriptions written by each physician who has a contracted with one or more of the health care plans affiliated with the PBM. PBMs administer prescription pharmaceutical claims, establish formularies, track physician prescribing patterns, provide education to improve their efficiency and cost effectiveness, and provide disease management programs. PBMs also seek to control the cost of prescription pharmaceuticals.

To lower the costs of prescription pharmaceuticals, PBMs negotiate prices on medications with pharmaceutical manufacturers. PBMs then determine price-performance profiles for every pharmaceutical on the market. Given that different pharmaceutical companies negotiate different prices with pharmaceutical manufacturers, the resulting price-performance profiles necessarily vary. For example, two pharmaceuticals for the treatment of high blood pressure will likely have two different price-performance profiles, each dependent upon the price a PBM pays the pharmaceutical manufacturer for the pharmaceutical.

Depending on its price-performance profile, a PBM will assign a status to each pharmaceutical on that PBM's formulary list. Typically, and by way of example, the statuses will be: preferred, approved, approved with prior authorization by the health insurance provider, available only if dispensed as a generic, and not approved. A pharmaceutical that has no formal status on a formulary or that has a "not approved" status is considered to be "off-formulary." The status of any particular pharmaceutical will, therefore, determine whether and to what extent a patient's health care plan will pay for the purchase of that pharmaceutical.

In addition to this use of formularies, some health care plans also provide physicians with a monthly pharmaceutical budget, financially penalizing physicians who go over budget and rewarding those physicians who are under budget. This is commonly referred to as "risk sharing" or "risk pooling."

For any number of reasons, PBMs revise their formularies frequently. As a result, there are often changes to the formulary that the patient and his physician may not be aware of. Thereafter, the patients might learn of the change only when advised by their pharmacist, or when they collect their prescription medication and notice a difference. Due to this late notice, there is frequently insufficient time to appeal or otherwise respond to the change.

PBMs communicate their formularies to physicians by mailing them binders containing formulary information every three to six months. Each health care plan has its own formulary so a physician may receive as many as one hundred different binders, though twenty to thirty is more typical. The content of the formulary is reinforced by a PBM "detail" force of PBM representatives who visit the physician periodically. Despite possessing the binders and the efforts of the "detail" force, physicians typically have a low compliance with the formularies.

For the most part, PBMs enforce their formularies at the pharmacy. When a patient submits a prescription, the pharmacist uses an on-line system to verify that the medication is listed on the patient's health care plan's formulary. If the medication is on-formulary, the pharmacy dispenses it, generally with a small co-payment by the patient. If it is off-formulary, and the prescribing physician has not authorized a generic substitute or a generic substitute does not exist, the patient either pays for the medication himself or the pharmacist calls the prescribing physician's office to request an alternative. This process is time consuming, and it requires the patient either to wait in the pharmacy or to return at a later time to obtain the medication.

Eventually, a patient with a chronic condition consumes the first supply of the prescribed medication. If the original prescription authorizes re-fills, the pharmacy will dispense a re-fill without further contact or authorization from the prescribing physician, assuming, of course, that the prescribed pharmaceutical remains listed on the formulary. If, however, the prescribed pharmaceutical is no longer listed on the formulary and the physician has not authorized a generic alternative, either the pharmacy must call the physician for a substitute or the patient must pay the full retail price for the off-formulary re-fill of the pharmaceutical (Under California law, PBMs must continue to pay for pharmaceuticals whose formulary status has changed). This process is repeated until the pharmacy dispenses the last authorized re-fill (if any), after which the patient or the pharmacy must contact the physician for a prescription renewal.

A renewal or re-prescription is a new prescription based at least in part upon the original prescription, i.e. for a pharmaceutical drug in the same therapeutic category (often the identical pharmaceutical drug), requiring a new authorization from the physician. While based on the therapeutic category of the pharmaceutical drug in the original prescription, the prescription renewal may change based upon revisions to the patient's insurance company's list of approved medications (the "formulary"), the patient's condition at the time of the renewal, or other factors.

Typically, a physician will have many patients with chronic health problems that require "chronic medications" (approximately 44%). As a result, substantial point-of-care inefficiencies arise in refilling and renewing prescriptions for chronic medications. Thus, on any given day, a physician will receive multiple calls requesting authorization for substitute pharmaceuticals that have changed formulary status in a re-fill or renewal situation. In the re-fill situation, the physician must take the time to determine an appropriate substitute that is on-formulary. In the renewal situation, the physician must take the time to evaluate several issues before authorizing a new prescription, namely: (1) whether the patient should continue taking the chronic medication; (2) whether to change any of the parameters of the prescription, e.g. brand or dosages; and/or (3) whether the chronic medication remains on-formulary and if not to identify a therapeutically equivalent pharmaceutical that is on-formulary.

In each case, the prescribing physician must deal with the inefficiencies attendant with the original prescription process, such as looking up the formulary status, dealing with a hardcopy of outdated formularies, reviewing the patient's records, etc. Additionally, because prescribing physicians typically must perform these duties at or very near the time of the pharmacy's telephone call, they are unable to address these issues efficiently, such as by addressing them in batches, verifying that a pharmaceutical is "preferred" by the PBM, etc.

These problems in dealing with formularies generate significant inefficiencies for the physician, and this translates into difficulties for PBMs seeking to control the costs for re-fill and renewal prescriptions. For example, physicians having to make rushed decisions when phoned for renewals are likely to default to the same chronic medication without checking the formulary to see if a different medication is now preferred by the PBM. Even if a chronic medication remains on-formulary, this is nonetheless a missed opportunity for a PBM to communicate its preferences to the prescribing physician because the physician has simply defaulted to the previously prescribed chronic medication without consulting the formulary list.

Preferred pharmaceuticals exist where PMBs have worked out special pricing or similar arrangements with pharmaceutical manufacturers. Therefore, despite the presence of more than a single medication on the formulary, PBMs might prefer one pharmaceutical over another. Even prescribing physicians who check the formulary are likely only to verify that the pharmaceutical is on-formulary, without determining whether that pharmaceutical is preferred by the PBM. Similarly, in the case of re-fills, a prescribing physician forced to determine an equivalent chronic medication that is on-formulary is not likely to determine whether a specific on-formulary pharmaceutical is preferred by the PBM over another therapeutically equivalent pharmaceutical.

Prescribing physicians have the responsibility to care for their patients, and, ultimately, they want to have more control over the decisions relating to their patient's care. PBMs and their formularies represent an intrusion into physicians' decision making processes and generate animosity among the physician community. As a result of this animosity, physicians are resistant to becoming more cooperative and compliant with the PBMs. This animosity, reluctance to comply with PBMs, and the missed communication opportunities between the PBMs and the prescribing physicians reduces compliance with formularies and decreases PBMs' flexibility to have more dynamic, cost efficient formularies.

Accordingly, there is a need in the art to increase the efficiency of using formularies at the point-of-care with a concomitant reduction of the intrusion in the decision-making process. Any improvement in the efficiency of the prescription renewal process would greatly assist in improving the overall efficiency of the prescription process as a whole. To this end, there is a need in the art for a system and/or method that will increase a physician's efficiency in handling renewal and/or refill prescriptions and allow the physician or the physician's staff to easily view prescription renewal request information. In addition, there is a need in the art for a system and/or method that will help the physician or the physician's staff to manage appointments with the physician's patients requiring prescription renewals.

SUMMARY OF THE INVENTION

The present invention provides a computer implemented method for providing prescription renewal request information via an electronic network. Upon receiving a request from a client (i.e., a prescriber, the prescriber's staff, or persons acting under the direction of these individuals) for generation of prescription renewal request information for a particular prescriber, a report is generated containing the requested renewal request information and transmitted to the client. The transmitted report containing renewal request information allows the client to easily review renewal request information and helps the client to manage appointments with patients whom the prescriber wishes to see.

Depending on the client request, the generated and transmitted report may be an "active renewals" page containing renewal request information regarding renewal requests that the prescriber has not yet reviewed, an "archived renewals" page containing renewal request information regarding renewal requests that the prescriber has already reviewed, an "appointment" page containing renewal request information regarding patients with whom the prescriber wishes to make an appointment, or a "prescription detail" page containing detailed renewal request information regarding a particular renewal request.

BRIEF DESCRIPTION OF THE DRAWINGS

For a better understanding of the nature and objects of the invention, reference should be made to the following detailed description, taken in conjunction with the accompanying drawings, in which:

FIG. 2 is a diagrammatic view of the dispenser memory shown in FIG. 1;

FIG. 3 is a diagrammatic view of the prescriber memory shown in FIG. 1;

FIGS. 11A-D are screen shots of a content Web-site containing prescription renewal request information according to an embodiment of the invention.

Like reference numerals refer to corresponding parts throughout the several views of the drawings.

DETAILED DESCRIPTION OF PREFERRED EMBODIMENTS

The present invention provides a means for renewing a pharmaceutical prescription via an electronic network. As used herein, a pharmaceutical is defined as any chemical substance used in the diagnosis, treatment, or prevention of a disease, illness, medical condition, or as a component of a medication. A pharmaceutical may further be defined as any therapeutic product used in medicine, or a drug derived from organic or inorganic chemicals and used to treat a wide range of medical conditions.

Figure 1:
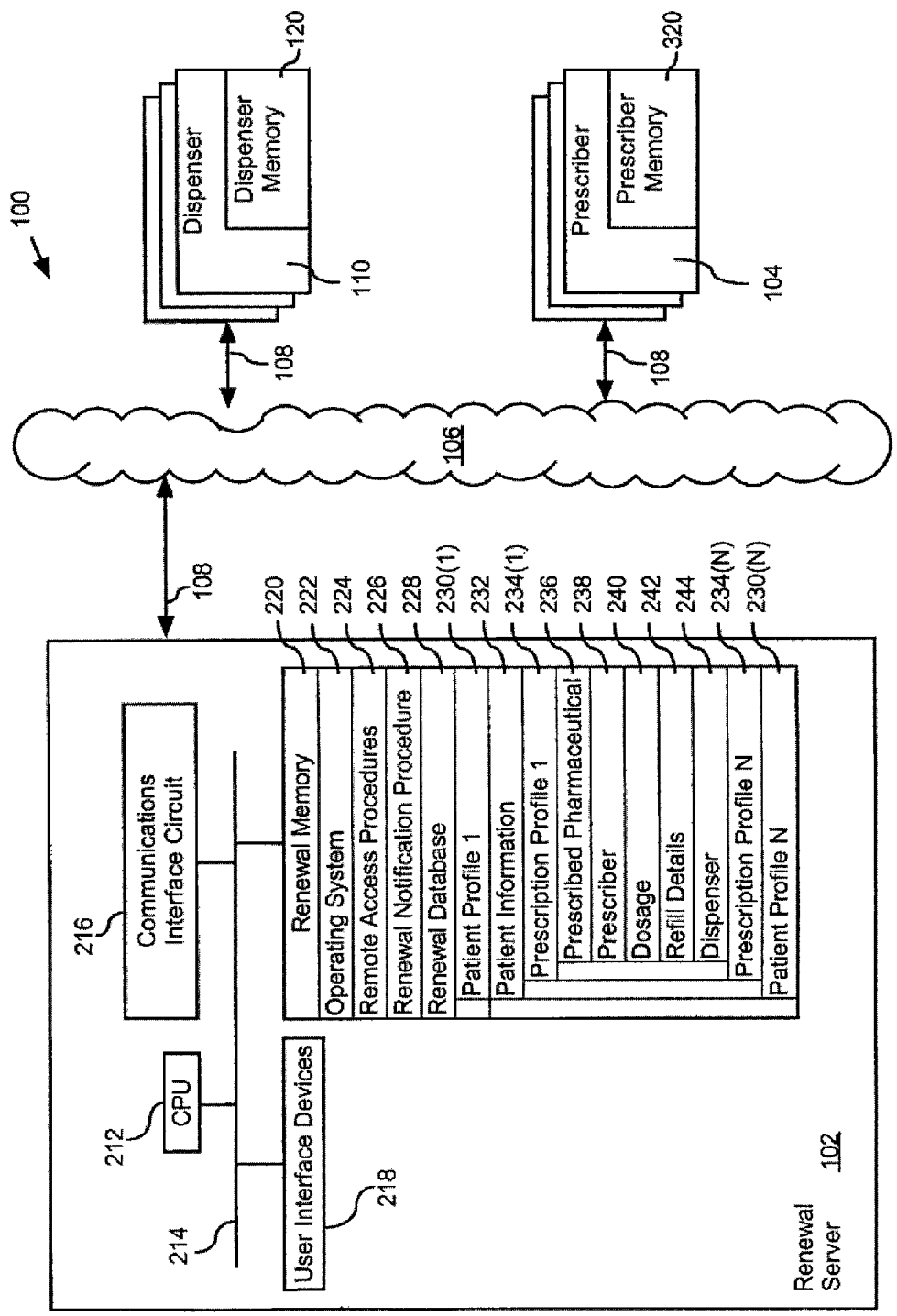
FIG. 1 is a diagrammatic view of an electronic network for renewing prescriptions in accordance with an embodiment of the present invention.

FIG. 1 is a diagrammatic view of an electronic network 100 for renewing prescriptions in accordance with an embodiment of the present invention. The network 100 comprises a series of points or nodes interconnected by communication paths. The network 100 may interconnect with other networks, may contain subnetworks, and may be embodied by way of a local area network (LAN), a metropolitan area network (MAN), a wide area network (WAN), or a global network (the Internet). The network 100 may further be characterized by the type of access service used, such as PSTN (Public Switched Telephone Network), ISDN (Integrated Services Digital Network), DSL (Digital Subscriber Line), ATM (Asynchronous Transfer Mode), T-carrier system, etc. In addition, network 100 may be characterized by the type of protocols used on it, such as WAP (Wireless Application Protocol), TCP/IP (Transmission Control Protocol/Internet Protocol), NetBEUI (NetBIOS Extended User Interface), or IPX/SPX (Internetwork Packet Exchange/Sequenced Packet Exchange). Additionally, the network 100 may be characterized by whether it carries voice, data, or both kinds of signals; by who can use the network 100 (whether it is public or private); and by the usual nature of its connections (e.g. dial-up, dedicated, switched, non-switched, or virtual connections).

The network 100 connects a plurality of pharmaceutical dispensers 110 and authorizing prescribers 104 to at least one renewal server 102. This connection is made via a communication or electronic network 106 that, as mentioned previously, may comprise an Intranet, wireless network, or preferably the Internet. The connection is made via communication links 108, which may, for example, be coaxial cable, copper wire (including PSTN, ISDN, and DSL), optical fiber, wireless, microwave, or satellite links. Communication between the prescriber, dispenser, and the renewal server preferably occurs via Internet protocol (IP) or an optionally secure synchronization protocol, but may alternatively occur via electronic mail (email).

As used herein, a dispenser is a retail-store pharmacy, a mail-order pharmacy, an online pharmacy, a PBM acting as a pharmacy, a PBM acting in conjunction with any of the former, or any entity or person authorized to dispense prescription pharmaceuticals. As used herein, an authorizing prescriber is a person having the authority to authorize a dispenser to dispense a pharmaceutical. Depending on the laws of any particular jurisdiction, such a person includes, without limitation, physicians, physician assistants, registered nurses, or persons acting under the direction of these individuals.

The renewal server 102 is shown in FIG. 1, and is described below as being distinct from the dispensers 110. The skilled artisan will, however, appreciate that the renewal server 102 and the dispensers 110 may be one and the same without deviating from the scope of the present invention.

The renewal server 102 comprises at least one data processor or central processing unit (CPU) 212, a renewal memory 220, user interface devices 218, a communications interface circuit 216, and at least one bus 214 that interconnects these elements. The renewal memory 220 includes an operating system 222 (such as DOS, UNIX™, Windows™, Linux™, OS/2™, AS/400™, PalmOS™, AIX™, NEXTSTEP™, OS/390™, OS/9™, OS/9000™, VMS™, CP/M™, Solaris™, or MacOS™), which stores instructions for communicating, processing data, accessing data, storing data, searching data, etc. The renewal memory 220 also includes remote access procedures 224 and a renewal notification procedure 226. The remote access procedures 224 are used for communicating (transmitting and receiving) data between the renewal server 102 and the electronic network 106.

The renewal memory 220 further includes a renewal database 228 preferably containing a plurality of patient profiles 230(1) to 230(N). Each patient profile 230(1) to 230(N) preferably contains patient information 232, such as contact details, information concerning the patient's medical history, the patient's medical insurance details, etc. Preferably, each patient profile 230(1) to 230(N) also contains a number of prescription profiles 234(1) to 234(N) for that particular patient. Each prescription profile 234(1) to 234(N) also preferably contains information such as a prescribed pharmaceutical identifier 236, a prescriber identifier 238, the dosage 240 of the prescribed pharmaceutical, refill details 242, and a dispenser identifier 244. An identifier is any means serving to identify, indicate, or name a body of data.

The dispensers 110 and prescribers 104 access the communication network 106 via remote client computing devices, such as desktop computers, laptop computers, notebook computers, handheld computers, personal digital assistants (PDA's), or the like. The prescribers 104 preferably use PDA's, as they are typically not desk bound, while dispensers 110 typically use desktop computers. The PDA's are preferably wireless, but may alternatively synchronize with a desktop computer that is itself connected to the communication network or may themselves connect to the communication network 106 via a wired connection.

The dispensers' and prescribers' computing devices, 110 and 104 respectively, preferably also include a data processor or central processing unit (CPU), user interface devices, communications interface circuits, and buses, similar to those described in relation to the renewal server 102. The dispensers 110 and the prescribers 104 also include memories 120 and 320 respectively, described below. Memories 220, 120, and 320 may include both volatile memory, such as random access memory (RAM), and non-volatile memory, such as a hard-disk.

FIG. 2 is a diagrammatic view of the dispenser memory 120 shown in FIG. 1. The dispenser memory 120 includes an operating system 122 and remote access procedures 124 compatible with the remote access procedures 224 (FIG. 1) in the renewal server's memory 220 (FIG. 1). Preferably, the dispenser memory 120 also includes a prescription filling procedure 126 for receiving electronic prescription requests and filling such requests (prescriptions and refills thereof). Furthermore, the dispenser memory 120 preferably also includes a dispenser database 128 containing a plurality of prescriptions identified by unique prescription identifiers 130(1) to 130(N). Each prescription 130(1) to 130(N) preferably contains patient information 132, such as contact details, information concerning the patient's medical history/records, the patient's medical insurance details, the patient's physician(s), etc. Each prescription 130(1) to 130(N) also preferably contains a pharmaceutical identifier 134, a prescribed dosage 136 for the prescribed pharmaceutical, a prescriber identifier 138, refill details 140, and renewal details 142. The refill details 140 preferably include the number of refills remaining and the date the last refill will be consumed and a date at which the refill will expire. The renewal details 142 preferably include a renewal date and a date at which the renewal will expire.

The dispenser memory 120 preferably also includes a formulary database 146 and a drug-drug reaction database 148, or a pointer thereto. Formulary database 146 includes, for example and without limitation, pharmaceutical identifiers and their associated formulary status (preferred, on-formulary, generic substitute permitted, or off-formulary).

FIG. 3 is a diagrammatic view of the prescriber memory 320 shown in FIG. 1. The prescriber memory 320 includes an operating system 322 and remote access procedures 324 compatible with the remote access procedures 224 (FIG. 1) in the renewal server's memory 220 (FIG. 1). The prescriber memory 320 preferably also includes a renewal authorization procedure 326 for creating and transmitting an authorized prescription renewal. The prescriber memory 320 preferably also include a renewal database 328 containing a plurality of patient profiles 330(1) to 330(N). Each patient profile 330(1) to 330(N) preferably contains patient information 332, such as contact details, information concerning the patient's medical history, the patient's medical insurance details, the patient's physician(s), and the like.

Each patient profile 330(1) to 330(N) also preferably contains a number of prescription profiles 334(1) to 334(N) for that patient. Each prescription profile 334(1) to 334(N) preferably contains information such as a prescribed pharmaceutical identifier 336, a prescriber identifier 338, the prescribed dosage 340 for the pharmaceutical, refill details 342, and a dispenser identifier 344. As described in co-pending application Ser. No. 09/487,932 filed Jan. 20, 2000, which is incorporated in its entirety herein by reference, the prescriber memory 320 preferably also includes a formulary database 350 and a drug-drug reaction database 352. The formulary database 350 and a drug-drug reaction database 352 are periodically updated by the renewal server.

It should be noted that the various databases described above have their data organized in a manner so that their contents can easily be accessed, managed, and updated. The databases may, for example, comprise flat-file databases (a database that takes the form of a table, where only one table can be used for each database), relational databases (a tabular database in which data is defined so that it can be reorganized and accessed in a number of different ways), or object-oriented databases (a database that is congruent, with the data defined in object classes and subclasses). The databases may be hosted on a single server or distributed over multiple servers. For ease of explanation, prescription data fields in any of the abovementioned databases will be referred to as prescription records.

Figure 4:
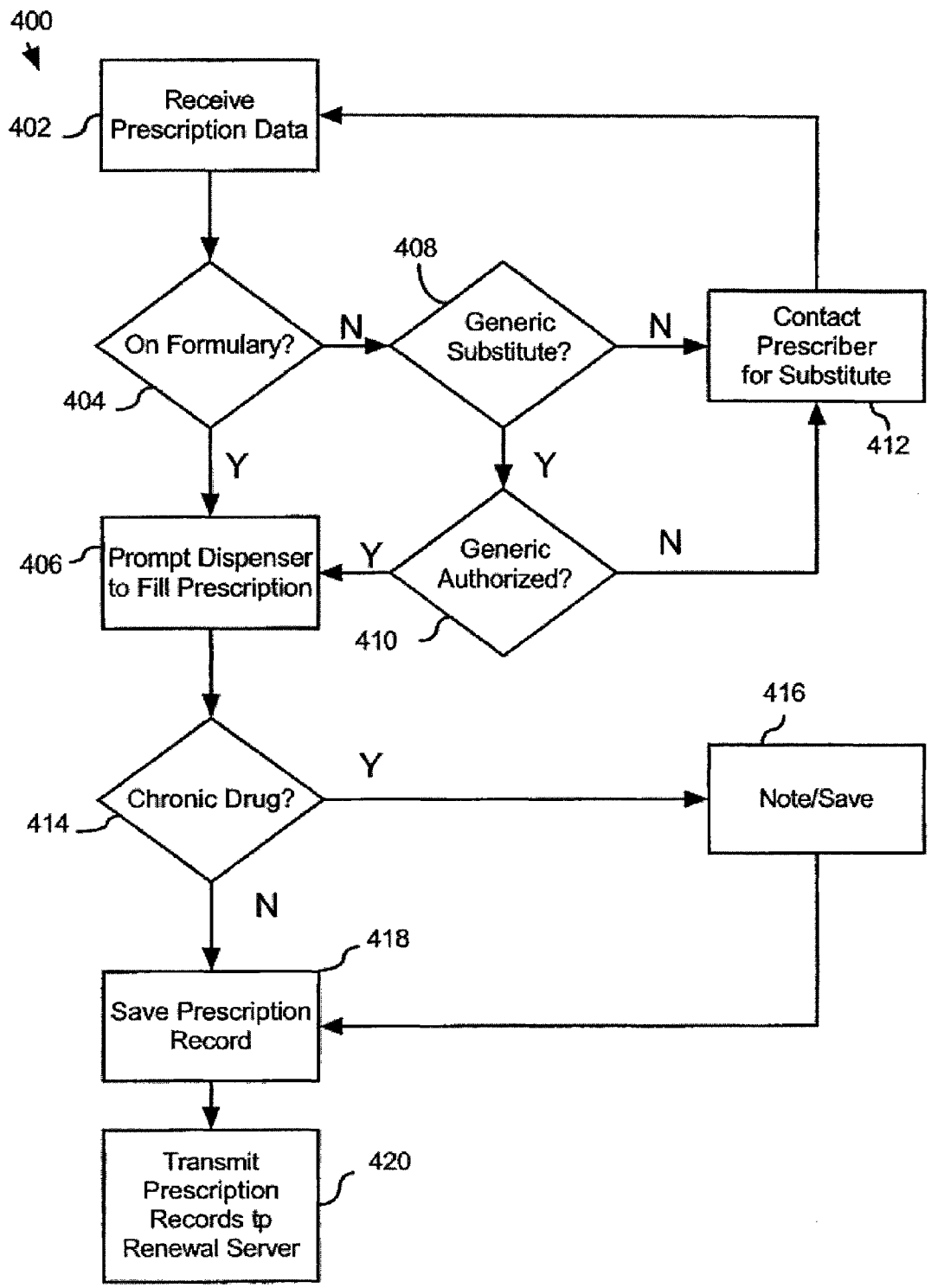
FIG. 4 is a flow chart showing a dispenser side method for filling original prescriptions in accordance with an embodiment of the present invention.

FIG. 4 is a flow chart showing a dispenser side method 400 for filling original prescriptions in accordance with an embodiment of the present invention. The prescription filling procedure (126 of FIG. 2) begins by receiving, at 402, an original prescription containing prescription data, including at least a pharmaceutical identifier, a patient identifier, a prescriber identifier, the prescribed pharmaceutical dosage, and refills details. Receipt of the original prescription may occur in a number of ways, such as electronically, by fax machine, by email, by postal mail, or by hand.

If the original prescription is received by hand, the details of the original prescription are captured manually and stored in the dispenser database (128 of FIG. 2), where the prescription is referenced by a unique prescription identifier (130 of FIG. 2). If the original prescription is received electronically, it is preferably captured automatically and stored in the dispenser database (128 of FIG. 2), where the prescription is referenced by a unique prescription identifier (130 of FIG. 2).

The formulary status of the prescribed pharmaceutical is then checked, at 404, by' referencing the formulary database (146 of FIG. 2). If the prescribed pharmaceutical is on the formulary list, the dispenser will be prompted, at 406, to dispense the pharmaceutical in accordance with the prescription. If the prescribed pharmaceutical is not on the formulary list, the procedure checks, at 408, whether a generic substitute is on the formulary list, at 408, and if a generic substitute is on the formulary list, whether the prescriber has authorized the use of a generic substitute, at 410. If a generic substitute is not on the formulary list or if the prescriber has not authorized a generic substitute, a notice is posted to contact the prescriber and request that he prescribe a substitute pharmaceutical, at 412.

After the original prescription has been filled, it is determined whether the prescribed pharmaceutical is a chronic medication, at 414. If the prescribed pharmaceutical is a chronic medication, the renewal method according to the invention notes and saves this fact, at 416. The prescription records in the dispenser database (128 of FIG. 2) are then updated, at 418. The updated prescription records are finally transmitted to the renewal server, at 420.

Figure 5:
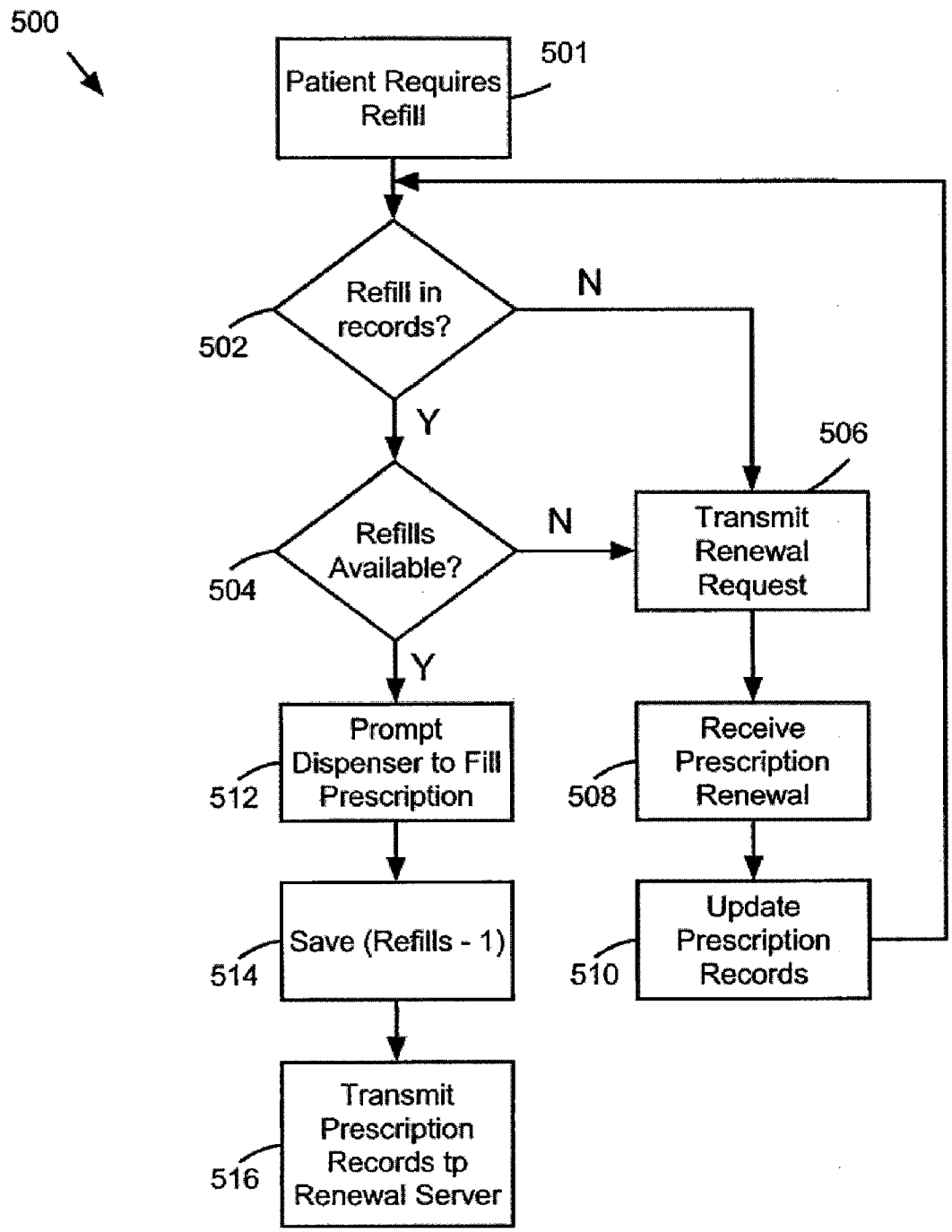
FIG. 5 is a flow chart showing a dispenser side method for filling a refill and authorized prescription renewals in accordance with an embodiment of the present invention.

FIG. 5 is a flow chart showing a dispenser side method 500 for filling refills and authorized prescription renewals in accordance with an embodiment of the present invention. When a patient orders a refill at a dispenser, at 501, the prescription filling procedure (126 of FIG. 2) checks, at 502, whether that refill prescription exists in its records. If the refill prescription exists, the prescription filling procedure checks whether there are any refills remaining available on that particular prescription, at 504.

If there is no refill prescription in the records, or if no refills remain on the prescription, the dispenser transmits a renewal request to the renewal server, at 506, i.e. a prescription renewal request is created before the expiration of the original or prior prescription. The prescription renewal request preferably includes a patient identifier, a pharmaceutical identifier, a dispenser identifier, a prescription identifier, a prescriber identifier, a dosage, number of refills, and a strength. Once prescribers authorize a prescription renewal, discussed in relation to FIG. 7, the dispenser receives the prescription renewal, at 508, and updates its prescription records, at 510.

If a refill is available, the dispenser is prompted to fill the prescription, at 512. The system then deducts one refill from the total amount of refills prescribed and saves this information, at 514, in the prescription records in the prescription database (128 of FIG. 2). The dispenser then transmits the updated prescription records to the renewal server, at 516.

Figure 6:
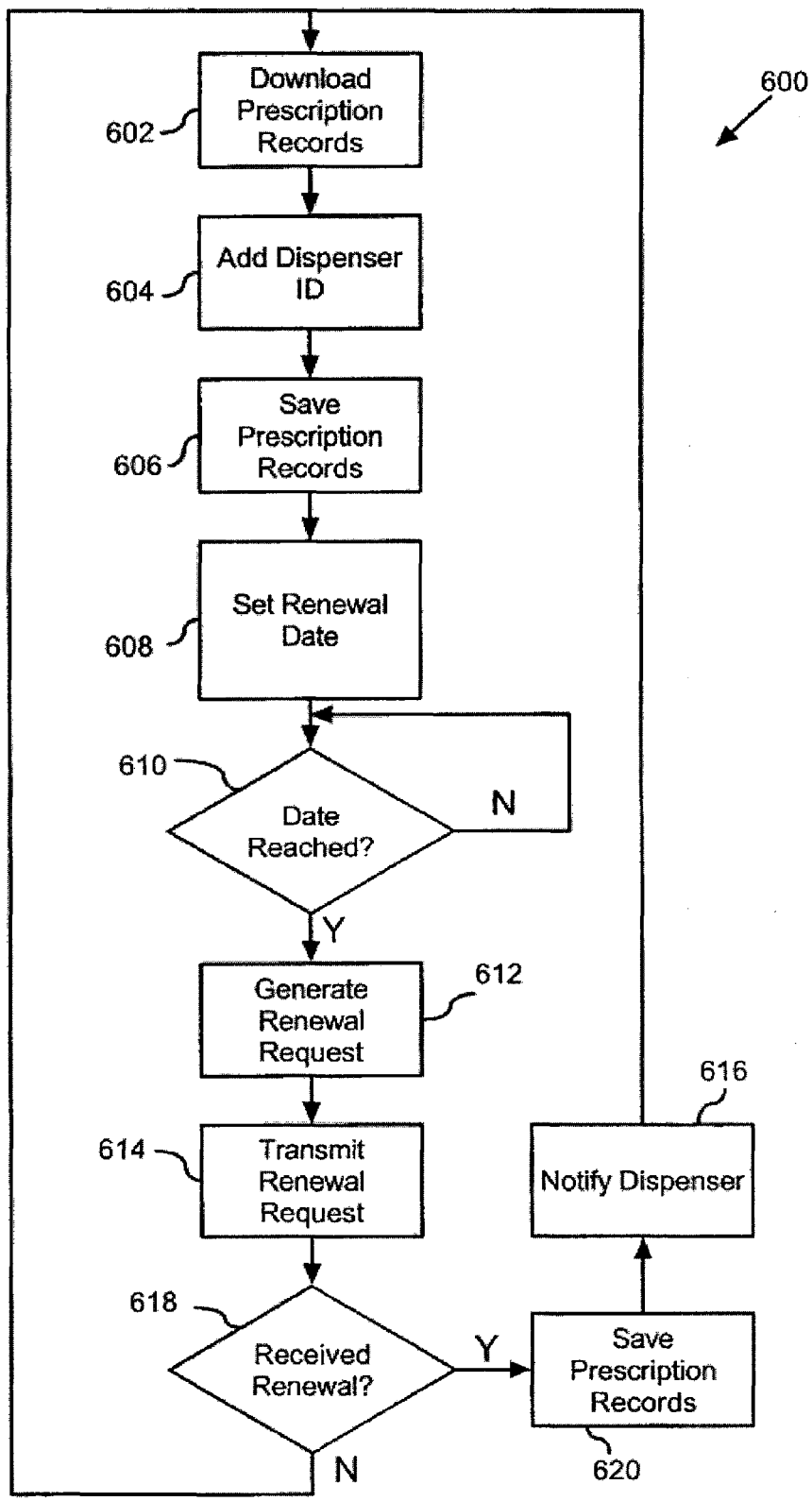
FIG. 6 is a flow chart showing a renewal server side method used to generate and transmit a request for a prescription renewal in accordance with an embodiment of the present invention.

FIG. 6 is a flow chart showing a renewal server side method 600 used to generate and transmit a request for a prescription renewal in accordance with an embodiment of the present invention. The renewal notification procedure (226 of FIG. 1) downloads, at 602, current prescription records from the dispenser (110 of FIG. 1) and saves the prescription records to the renewal database (230 of FIG. 1). The renewal database adds a dispenser identifier (246 of FIG. 1) to the prescription records, at 604. The prescription records are then saved to the renewal database, at 606.

The renewal notification procedure then calculates when the prescribed refills will run out, and sets a renewal date a set time prior to the date when the prescribed refills will run out, such as three weeks before such a date. The renewal notification procedure then periodically determines whether the renewal date has been reached, at 610. Once the renewal date has been reached, a prescription renewal request is generated, at 612, and transmitted to the prescriber responsible for prescribing the original prescription, at 614, or any other prescriber specified. Safety precautions are preferably incorporated so as to avoid a single renewal request being sent to multiple prescribers. The prescriber then deals with the renewal request as discussed in relation to FIG. 7. Once the prescriber has renewed a prescription and transmitted the renewed prescription back to the renewal server, it is received, at 618, and the new renewal details are saved into the prescription records, at 620. The dispenser is then notified to fill the prescription renewal, at 616. It should be noted that refills, renewal requests, and prescription renewals preferably expire after a predetermined time period.

Figure 7:
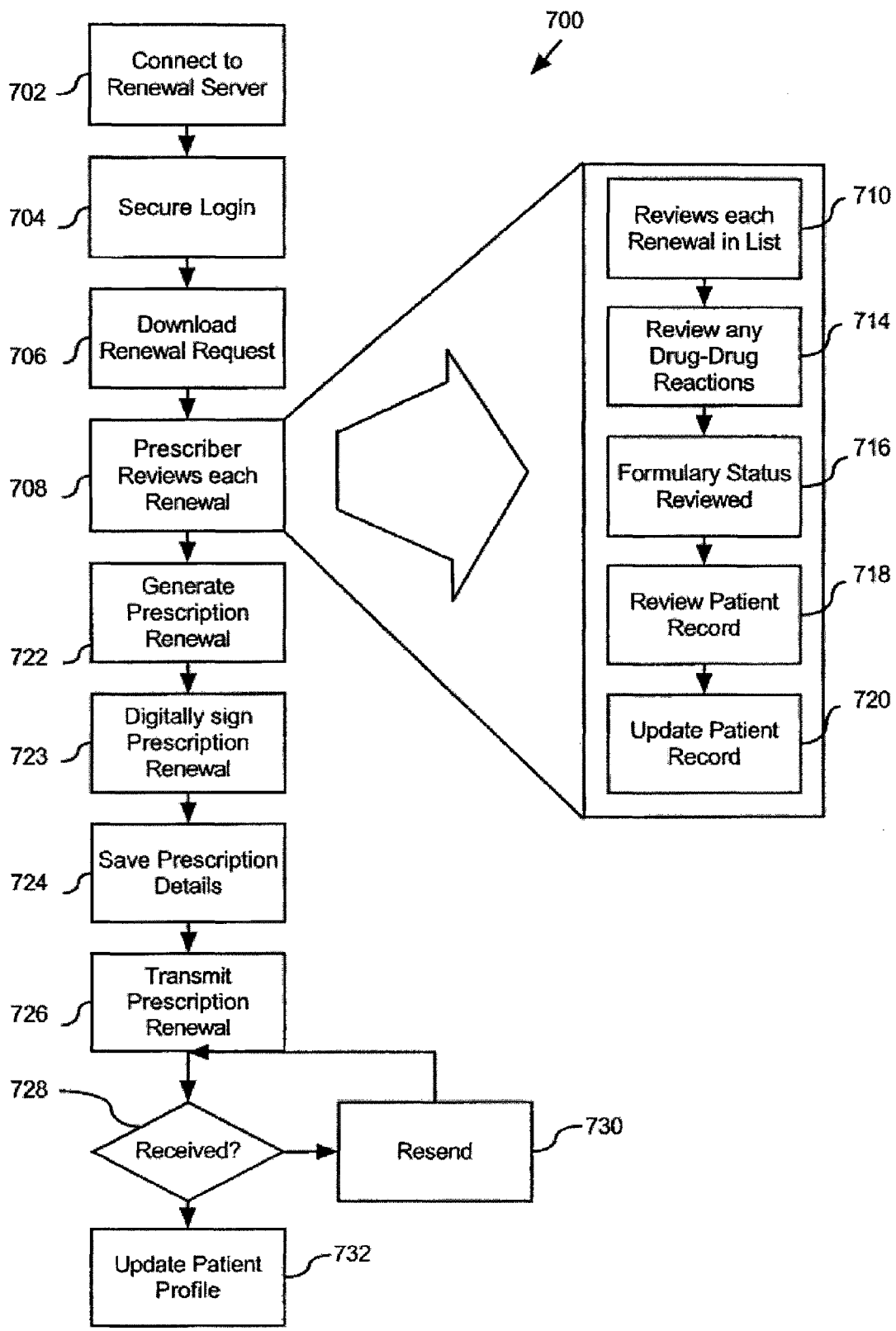
FIG. 7 is a flow chart showing the prescriber side method for authorizing a prescription renewal in accordance with an embodiment of the present invention.

FIG. 7 is a flow chart showing a procedure for authorizing a prescription renewal in accordance with an embodiment of the present invention. The prescriber (104 of FIG. 1) connects to the electronic network (106 of FIG. 1), more specifically the renewal server (102 of FIG. 1), at 702. The prescriber then securely logs into the renewal server, at 704. Preferably, the secure login occurs automatically when the prescriber synchronizes his PDA with his desktop computer, but may also occur manually by having the prescriber enter a unique username and password or digital certificate and secret signing key, or the like.

The prescriber's computing device (104 of FIG. 1) then downloads, preferably automatically during synchronization, all renewal request(s) directed to that prescriber, at' 706. The prescriber may at this time, or at any other time between successive synchronizations, review the renewal requests, at 708, and deal with the requests in a batch mode or, if preferred, piecemeal.

In addition to reviewing the information provided in the renewal request itself, at 710, additional information may be provided to the prescriber to assist in the decision making process. The renewal authorization procedure (326 of FIG. 3) displays such additional information using a prescribed pharmaceutical identifier (336 of FIG. 3), a patient profile (330 of FIG. 3), and/or a dispenser identifier (344 of FIG. 3). The additional information preferably includes, without limitation, a drug-drug reaction database (354 of FIG. 3), at 714, a formulary database (350 of FIG. 3), at 716, patient medication history, and/or low cost therapeutic alternatives. It will be recognized that these databases may be separate or combined.

Alternatively, additional information may be added to the renewal request by the renewal server (102 of FIG. 1) and transferred to the prescriber therewith. The formulary database (350 of FIG. 3) then preferably provides the prescriber with generic substitutes, brand name substitutes, and/or PBM preferences in addition to the formulary status of the pharmaceutical prescribed in the prescription up for renewal.

Additionally, the patient identifier and/or the unique prescription identifier points to the patient profile (330 of FIG. 3) that will provide the prescriber with relevant patient information, such as previous prescriptions, or comments and notes useful to the prescriber, at 718. If the prescriber makes any changes, the patient's medical profile is updated, at 720. As part of the review process, the prescriber may want to, or may be required to, contact the patient for further consultation, after which the prescriber may update that patient's profile (330 of FIG. 3) with further comments. Contacting the patient may take the form of making a notation on the PDA, such as clicking on an "Ask patient to contact me" button, which ultimately is communicated to the renewal server. The patient is then contacted by back office staff, or alternatively the dispenser is contacted, to notify the patient to contact the prescriber. This may take the form of a telephone call, email, postal mail, facsimile, or the like.

A skilled artisan will recognize that the transfer of the renewal request 706 may occur using many different sets of steps other than those described above without deviating from the scope of the present invention. For example, and without limitation, the renewal server (102 of FIG. 1) could contact the prescriber's computing device or PDA to initiate the transfer of data. The ultimate result is that the prescriber has the renewal request(s) in an electronic format resident on his computer and/or PDA, such that the prescriber may review each notification at a time convenient and efficient for the prescriber.

After reviewing the renewal request, the renewal authorization procedure (326 of FIG. 3) generates an electronic prescription renewal, at 722. The electronic prescription renewal preferably includes at least a patient identifier, a pharmaceutical identifier, a prescribed dosage, a prescriber identifier, and refill details. It should be noted that the renewed prescription may have different components to the prior prescription initially prescribed. The prescriber then authorizes the prescription renewal using a digital signature, typically using an algorithm such as that provided by Certicom™ 723, and the record is saved in an authorized prescription renewal database (328 of FIG. 3), at 724.

The authorized prescription renewal is then transmitted to the renewal server for further processing, at 726. The renewal authorization procedure (326 of FIG. 3) waits for a notification from the renewal server that the authorized prescription renewal was in fact received, at 728. If it was not, the prescriber is prompted to rectify the situation (e.g., resend the prescription renewal or call the renewal server service directly), at 730. If it was received, the patient profile (232 of FIG. 1) is updated accordingly. The prescriber then preferably notifies the patient that the renewal has been authorized.

The renewal server, prescriber, and/or dispenser periodically share updates of the status of the prescription renewal requests. The status is preferably ascertained by said renewal server which determines how many prescription renewal requests were transmitted to the prescriber and establishes how many of the prescription renewal requests the prescriber has reviewed. The status is then preferably sent by the renewal server to the prescriber.

It is anticipated that the prescriber will contact the renewal server periodically and download multiple renewal requests at one time for review at the prescriber's convenience. It is also anticipated that the prescriber will transmit multiple authorized prescription renewals, rather than a single renewal request, each time he completes a review. It is in this manner that the prescriber may receive multiple requests for prescription renewals without receiving telephone calls from patients or pharmacies, may review the requests batch-wise, may contact patients for consultations at times convenient to the prescriber, and may check formularies. Wireless technologies permit PDAs to electronically transfer the data without the need of a wired connection.

Figure 8:
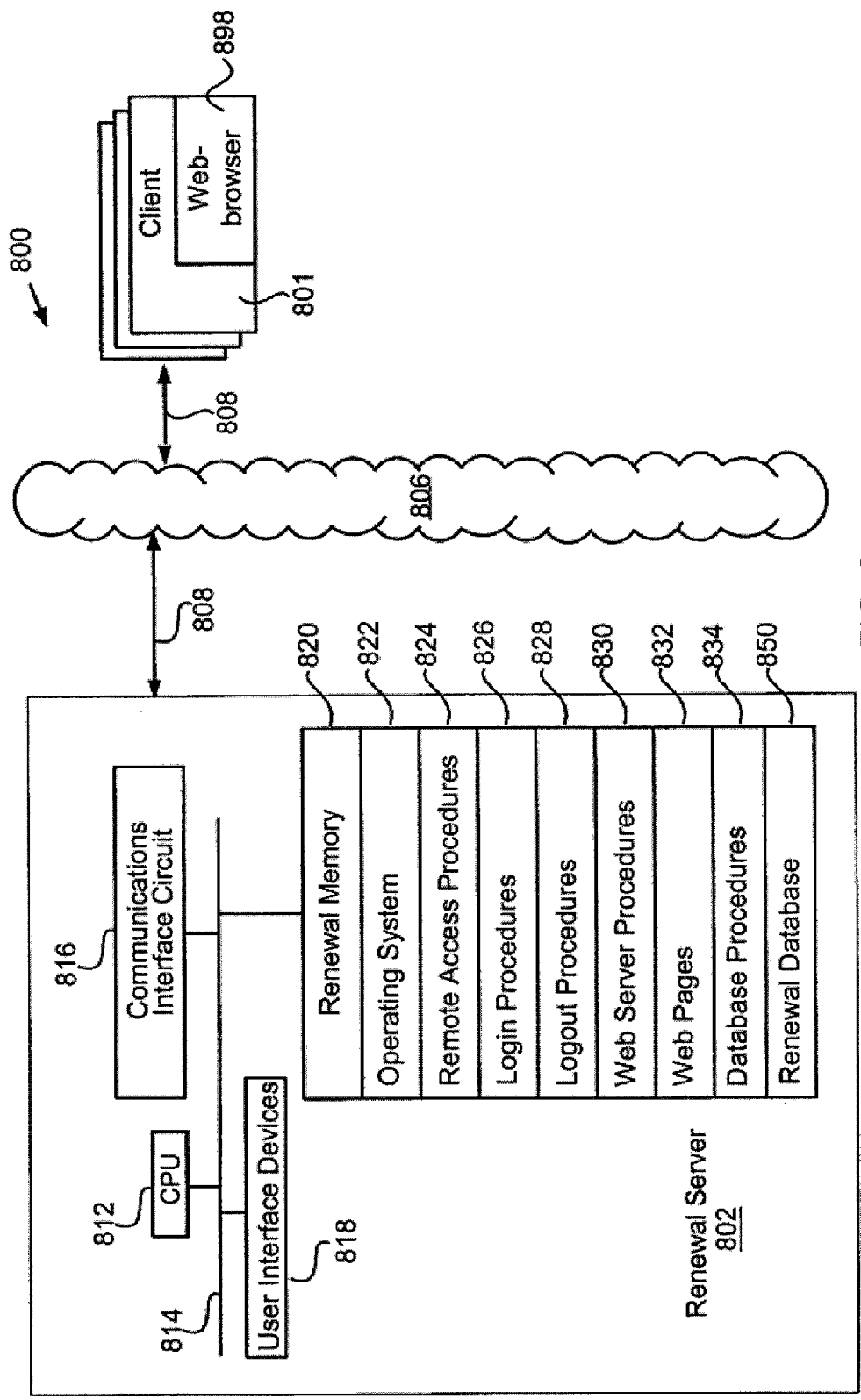
FIG. 8 is a diagrammatic view of an electronic network for generating and transmitting prescription renewal request information in accordance with the present invention.

FIG. 8 is a diagrammatic view of an electronic network 800 for generating and transmitting prescription renewal request information reports (hereinafter "renewal request information"). The electronic network 800 is similar to the electronic network 100 of FIG. 1 and further includes, in accordance with another embodiment of the invention, one or more client computing devices 801 that are accessed and used by one or more clients. As used herein, clients are people having the authority to access renewal request information and who access such information using a client computing device 801. Examples of clients are a prescriber, the prescriber's staff, and persons acting under the direction of these individuals. The electronic network 800 generates and transmits renewal request information in response to a client request for renewal request information pertaining to a particular prescriber.

The network 800 connects a plurality of client computing devices 801 to at least one renewal server 802. These connections are made via an electronic network 806 and communication links 808. The client and the prescriber may be the same entity and may also include, without limitation, the prescriber's staff or persons acting under the direction of these individuals.

The clients access the communication network 806 via remote client computing devices, such as desktop computers, laptop computers, notebook computers, handheld computers, personal digital assistants (PDA's), or the like. The clients preferably use desktop computers as they typically are desk bound in an office environment.

The client computing devices 801 preferably include a data processor or central processing unit (CPU), user interface devices, communications interface circuits, and buses, similar to those described in relation to the renewal server 802 (described below). The client computing devices 801 also include memories which may include both volatile memory, such as random access memory (RAM), and non-volatile memory, such as a hard-disk. In addition, the client computing devices 801 preferably include a Web browser 898, such as Netscape Navigator and Microsoft Internet Explorer, for browsing the World Wide Web and a modem to access the electronic network 806 (as is well understood in the art).

The renewal server 802 comprises at least one data processor or central processing unit (CPU) 812, a renewal memory 820, user interface devices 818, a communications interface circuit 816, and at least one bus 814 that interconnects these elements. The renewal memory 820 includes an operating system 822, remote access procedures 824, login procedures 826, logout procedures 828, Web-server procedures 830, Web pages 832, database management procedures 834, and a renewal database 850.

The login procedures 826 are a series of executable routines or programs that control the secure login of the clients into the renewal server 802. The logout procedures 828 are a series of executable routines or programs that control the logout of the clients from the renewal server 802.

The Web-server procedures 830 handle Web-page requests from a client's Web browser 898 and generate and transmit content in response to the requests. The Web-server procedures 830 also execute server-side scripts (Common Gateway Interface scripts (CGI), Active Server Page (ASP), JAVA Server Page (JSP), etc.) that provide functions, such as database searching. The Web pages 832 are World Wide Web-documents, typically text files coded in HTML, which may also contain JAVASCRIPT code or other commands. The database management procedures 834 handle the storing, retrieving, and updating of data held in the renewal database 850.

Preferably, the login procedures 826, logout procedures 828, Web-server procedures 830, and Web pages 832, contained in renewal memory 820 enable the renewal server 802 to provide World Wide Web-services on the Internet by sending and receiving electronic content to and from clients. Alternately, the login procedures 826, logout procedures 828, Web-server procedures 830, and Web pages 832 are contained on a Web server, external to renewal server 802, that provides World Wide Web-services on the Internet to clients by accessing the renewal database 850 of the renewal server 802.

Figure 9:
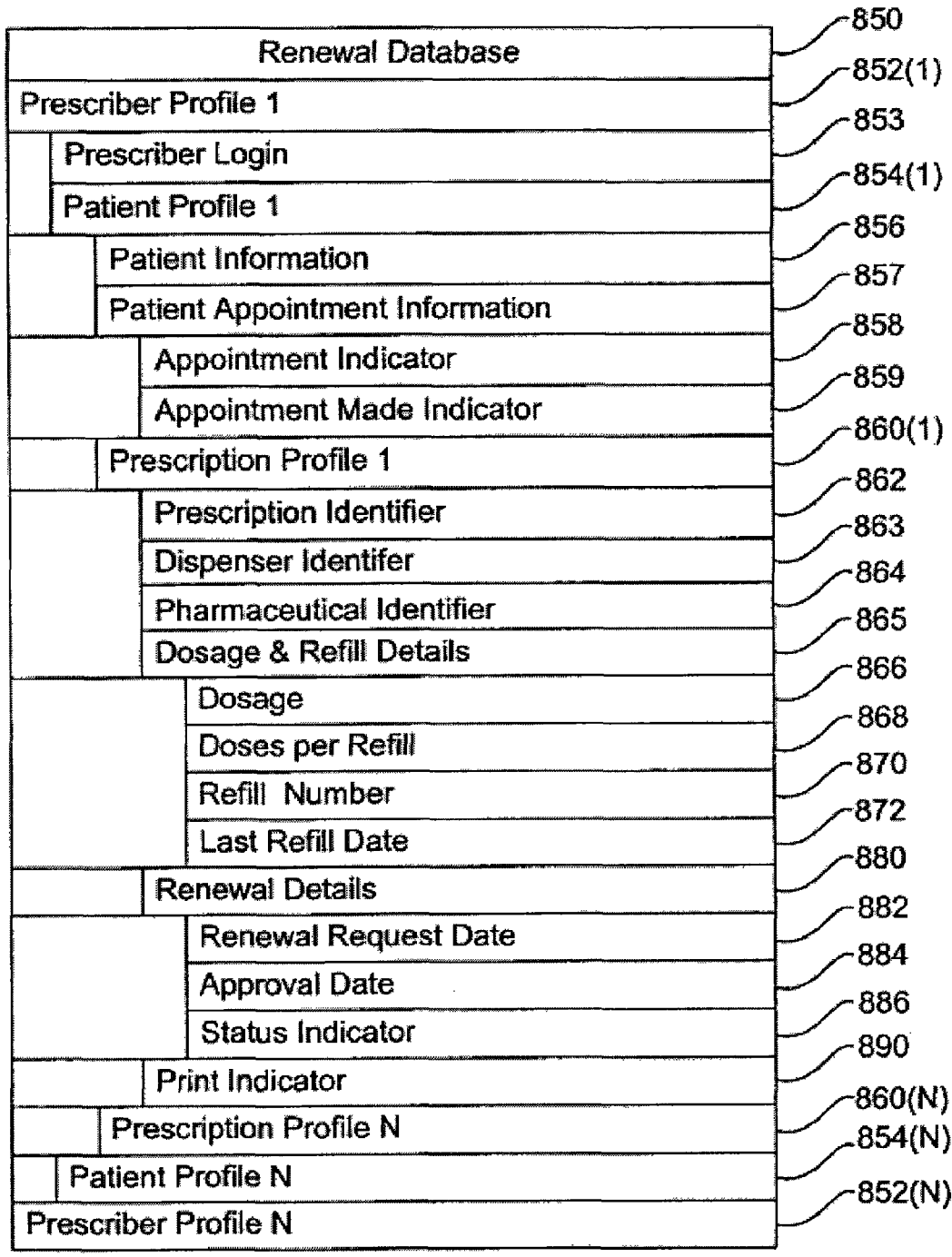
FIG. 9 is a diagrammatic view of the renewal database 850 shown in FIG. 8.

FIG. 9 is a diagrammatic view of the preferred renewal database 850 shown in FIG. 8. The renewal database 850 preferably contains a plurality of prescriber profiles 852(1) to 852(N). Each prescriber profile 852 preferably contains prescriber login information 853 and a plurality of patient profiles 854(1) to 854(N). Each patient profile 854 preferably contains patient information 856 pertaining to a particular patient, such as patient's name, date of birth, gender, and contact details. Each patient profile 854 also contains patient appointment information 857 such as an appointment indicator 858 indicating whether the prescriber wishes to make an appointment with the patient and an appointment made indicator 859 indicating whether an appointment has already been made with the prescriber. Preferably, each patient profile 854 also contains a plurality of prescription profiles 860(1) to 860(N) for the particular patient. Each prescription profile 860 preferably contains information such as an unique prescription identifier 862, a dispenser identifier 863, a pharmaceutical identifier 864, dosage and refill details 865, renewal details 880, and a print indicator 890 indicating whether a prescription detail page of a particular renewal request has been printed by a client.

The dosage and refill details 865 of the prescribed pharmaceutical preferably includes a dosage 866 of the prescribed pharmaceutical, a number of doses per refill 868, a number of refills 870, and a last refill date 872. The renewal details 880 for the prescribed pharmaceutical preferably includes a renewal request date 882, an approval date for the renewal request 884 (if any), and a status indicator of the renewal request 886 indicating whether the renewal request has been approved, not approved, or not yet reviewed by the prescriber. If the status indicator of the renewal request 886 indicates that the prescriber has approved or has not approved the renewal request, then the prescriber has reviewed the renewal request.

Therefore, each renewal request includes any or all information contained in the patient profile 854 regarding a request for a prescription renewal.

It should be noted that the database described above has its data organized in a manner so that its contents can easily be accessed, managed, and updated. The database may, for example, comprise a flat-file database (a database that takes the form of a table, where only one table can be used for each database), a relational database (a tabular database in which data is defined so that it can be reorganized and accessed in a number of different ways), or an object-oriented database (a database that is congruent, with the data defined in object classes and subclasses). The database may be hosted on a single server or distributed over multiple servers.

Figure 10A:
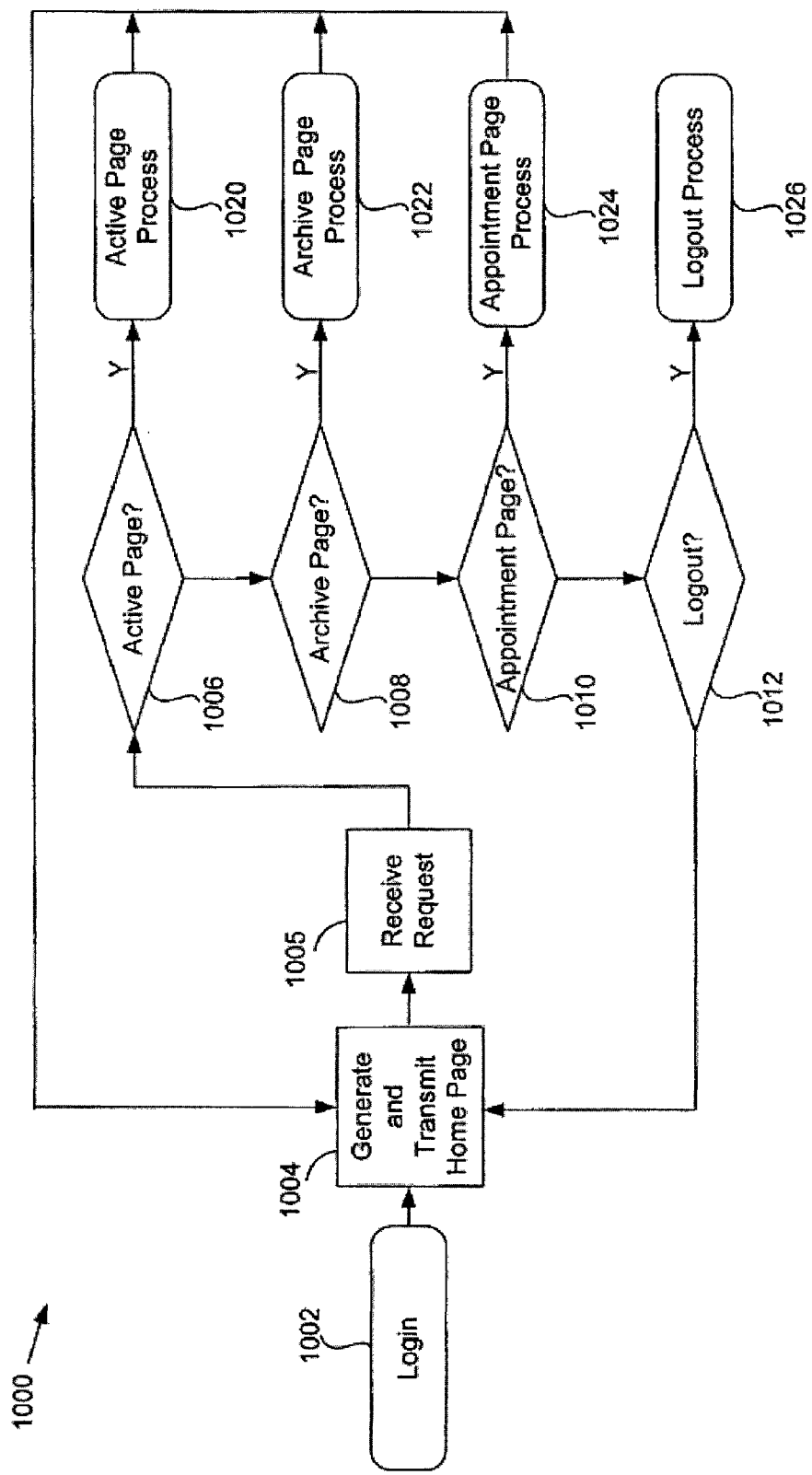
FIGS. 10A-E are flow charts of the renewal server process for generating and transmitting prescription renewal request information in accordance with the present invention.

FIG. 10A is a flow chart of the overall renewal server process 1000 for generating and transmitting renewal request information in response to receiving a client request for renewal request information pertaining to a particular prescriber. Using a client computing device 801, a client accesses the renewal server 802 (FIG. 8) via the electronic network 806 (FIG. 8). For example, the client using a Web browser 898 on the client computing device 801 accesses the renewal server 802 (FIG. 8) via the electronic network 806 (FIG. 8) using a dial-up or broadband Internet connection.

Once the client computing device 801 is connected to the renewal server 802 (FIG. 8), the login procedures 826 (FIG. 8) on the renewal server are invoked. The login procedures run a login process 1002 using a security protocol such as Netscape's SHTTP, NCSA's SHTTP, Microsoft's PCT or IETF's IPSec. The login procedures preferably generate and transmit a login web page to which the client responds on the client computing device 801, for example, by entering a unique username and password. The login procedures 826 (FIG. 8) then verify the username and password using the prescriber login information 853 (FIG. 9) in the renewal database 850 (FIG. 8). The database management procedures 834 then search the renewal database 850 (FIG. 8) to determine the prescriber profile 852 (FIG. 9) associated with the username supplied by the client.

Once the client has successfully logged into the renewal server 802 (FIG. 8), the Web-server procedures 830 (FIG. 8) generate and transmit, at 1004, a home page containing link buttons to an active renewals page, an archived renewals page, an appointment page, and to a renewal server logout procedure. As used herein, a link button is a linkage to a particular page which is downloaded onto the client computing device 801 (FIG. 8) upon selection.

The renewal server 802 (FIG. 8) then receives, at 1005, a Web-page request or query from the client's Web browser 898 (FIG. 8). Based on the Web-page request, the Web-server procedures 830 (FIG. 8) in the renewal memory 820 (FIG. 8) preferably determine at 1006, 1008, 1010, or 1012 whether the client wishes to view an active renewals page, an archived renewals page, an appointment page, or logout of the renewal server. In addition, the database management procedures 834 search the renewal database 850 (FIG. 8) to locate and retrieve renewal request information matching the Web-page request or query.

Figure 10B:
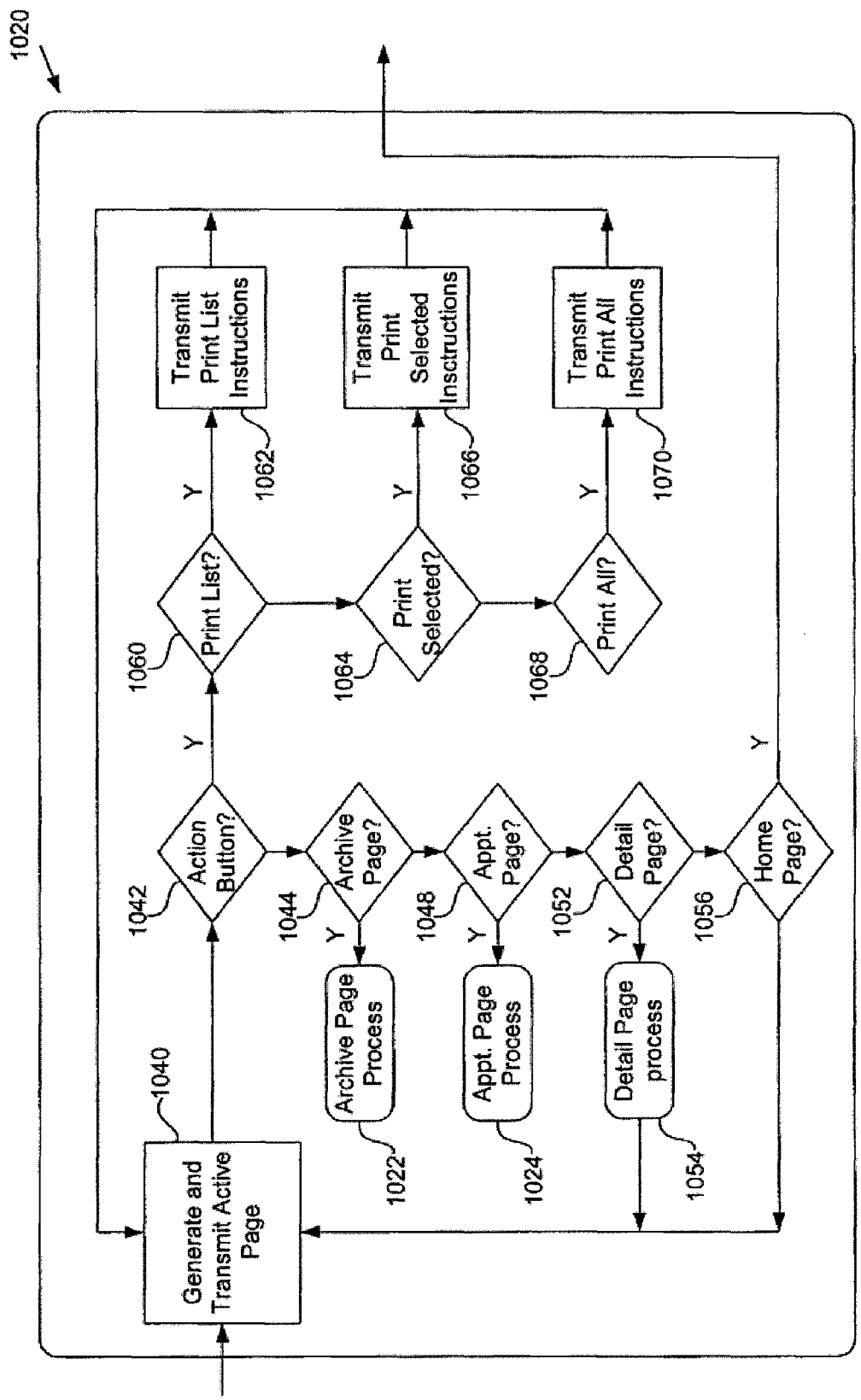

If the client wishes to view the active renewals page (1006—Yes), an active page process 1020, as shown in FIG. 10B, is followed. An example of an active renewals page is shown in FIG. 11A.

Figure 10C:
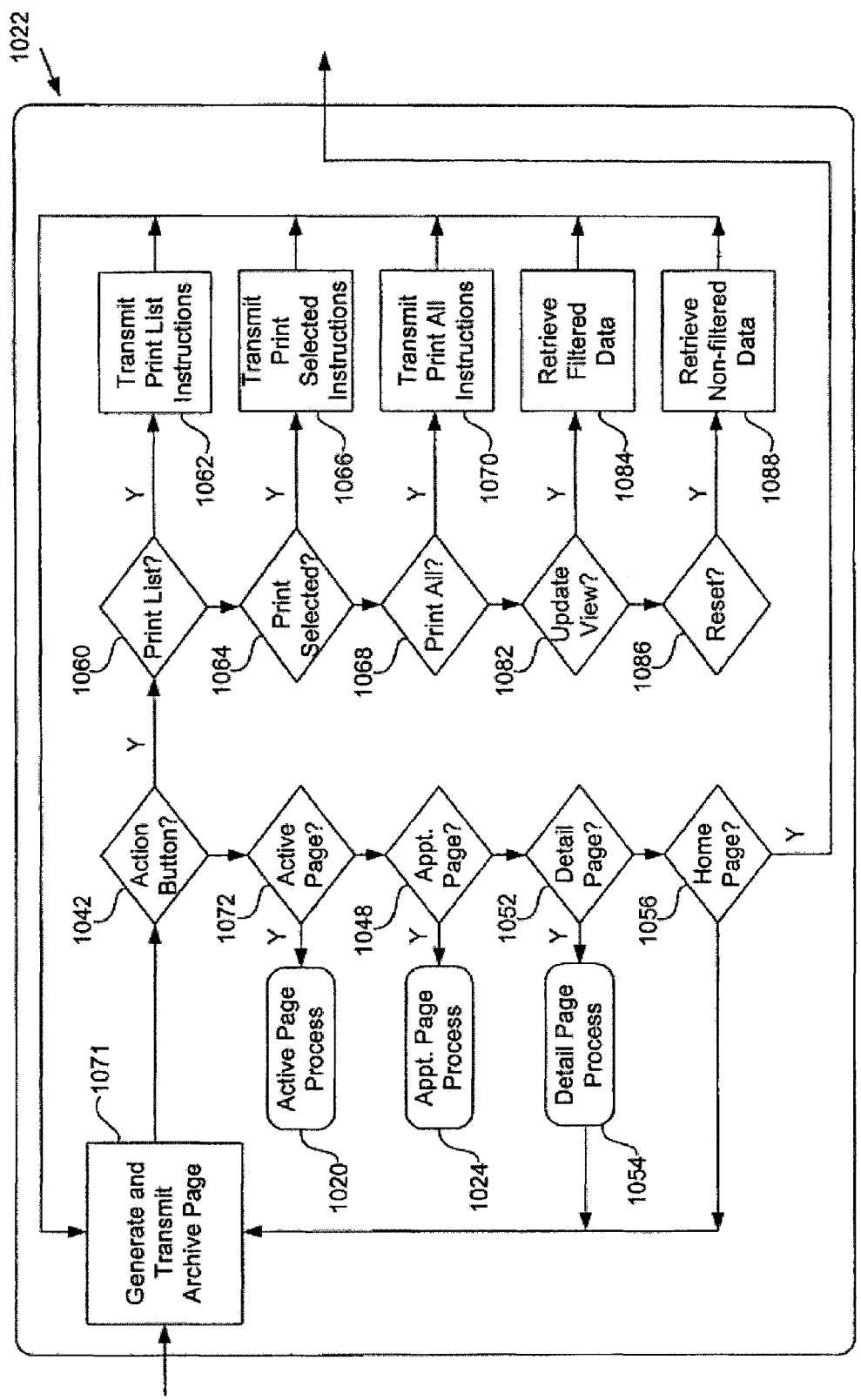

If it is determined that the client does not wish to view the active renewals page (1006—No), the Web-server procedures 830 (FIG. 8) then determine, at 1008, whether the client wishes to view an archived renewals page. If it is determined that the client wishes to view the archived renewals page, an archive page process 1022, as shown in FIG. 10C, is followed. An example of an archived renewals page is shown in FIG. 11B.

Figure 10D:
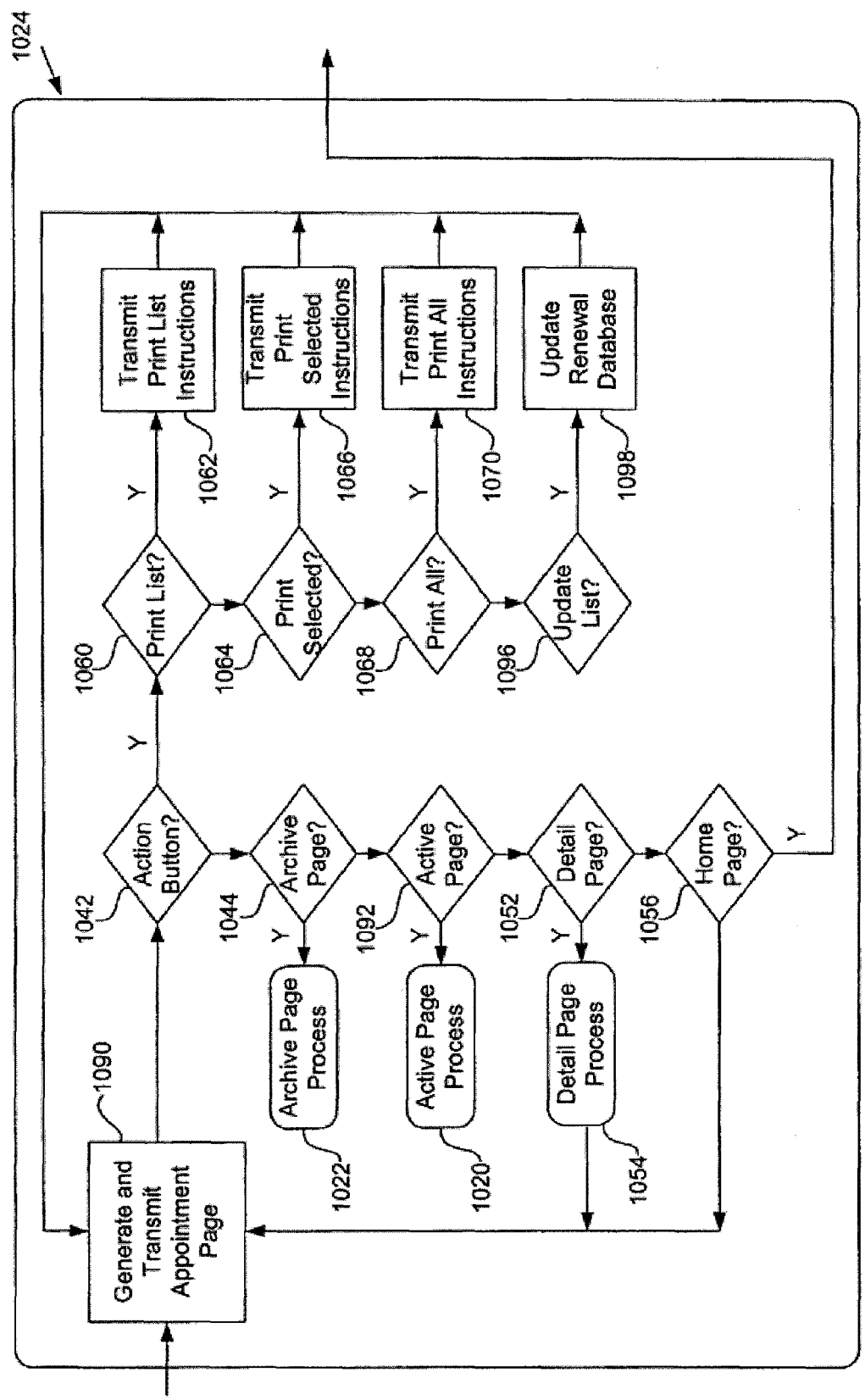

If it is determined that the client wishes to view the appointment page (1010—Yes), an appointment page process 1024, as shown in FIG. 10D, is followed. An example of an appointment page is shown in FIG. 11C.

If it is determined that the client wishes to log out of the renewal server (1012—Yes), the logout procedures 828 (FIG. 8) on the renewal server 802 (FIG. 8) are invoked. The logout procedures run a logout process 1026 where the client is logged out of the renewal server. If the client does not want to log out of the system (1012—No), the process is restarted and the home page is regenerated and retransmitted, at 1004. After the active renewals page process 1020, the archived renewals page process 1022, or the appointment page process 1024 has completed, the process is restarted and the home page is regenerated and retransmitted, at 1004.

FIG. 10B is a flow chart of the active page process 1020 of FIG. 10A. At 1040, the Web-server procedures 830 (FIG. 8) generate and transmit an active renewals page to the client computing device 801 (FIG. 8). The active renewals page contains information regarding renewal requests which have not yet been reviewed by the prescriber. An example of an active renewals page is shown in FIG. 11A. The active renewals page contains renewal request information pertaining to the prescriber identified by the login username.

The Web-server procedures then determine, at 1042, whether the client wishes to implement an action button. As used herein, action buttons are buttons which perform predefined functions upon selection and include, without limitation, print buttons, update buttons, a reset button, and a close button. Print buttons include individual buttons to perform various functions, for example, to print a list of all renewal requests contained on a current page, to print a prescription detail page of all renewal requests selected by a check box, or to print a prescription detail page of all renewal requests contained on a current page. Update buttons are used in conjunction with filter boxes to update the information viewed on a current page or with check boxes to update data stored in the renewal database 850 (FIG. 8). A reset button is used to reset the information viewed on a current page, and a close button is used to close a current page.

If it is determined that the client wishes to implement an action button (1042—Yes), it is then determined, at 1060, if the client wishes to implement a "print list" button. If so, the Web-server procedures 830 (FIG. 8) transmit, at 1062, instructions to the client computing device 801 (FIG. 8) to print a list of all renewal requests contained on the current page.

If it is determined that the client does not wish to implement the "print list" button (1060—No), it is then determined, at 1064, whether the client wishes to implement a "print selected" button. If so, the Web-server procedures transmit, at 1066, instructions to the client computing device 801 to print a prescription detail page of each renewal request selected by marking a check box on the current page. In addition, the database management procedures 834 (FIG. 8) update the print indicators 890 (FIG. 9) of each renewal request selected by a check box to indicate that a prescription detail page of each such renewal request has been printed by a client.

If it is determined that the client wishes to implement a "print all" button (1068—Yes), the Web-server procedures 830 (FIG. 8) transmit, at 1070, instructions to the client computing device 801 (FIG. 8) to print a prescription detail page of all renewal requests contained on the current page. In addition, the database management procedures 834 (FIG. 8) update the print indicators 890 (FIG. 9) of all renewal requests contained on the current page to indicate that a prescription detail page of each such renewal request has been printed by a client.

After the Web-server procedures 830 (FIG. 8) transmit, at 1062, instructions to print a list of all renewal requests contained on the current page, a prescription detail page of selected renewal requests 1066, or a prescription detail page of all renewal requests contained on the current page 1070, the process is restarted and the active renewals page is regenerated and retransmitted, at 1040.

If it is determined that the client does not wish to implement an action button (1042—No), the Web-server procedures 830 (FIG. 8) then determine at 1044, 1048, 1052, or 1056 whether the client wishes to view an archived renewals page, an appointment page, a prescription detail page, or the home page.

If it is determined that the client wishes to view the archived renewals page (1044—Yes), an archived renewals page process 1022 is followed, as shown in FIG. 10C. If it is determined that the client wishes to view the appointment page (1048—Yes), an appointment page process 1024 is followed, as shown in FIG. 10D.

Figure 10E:
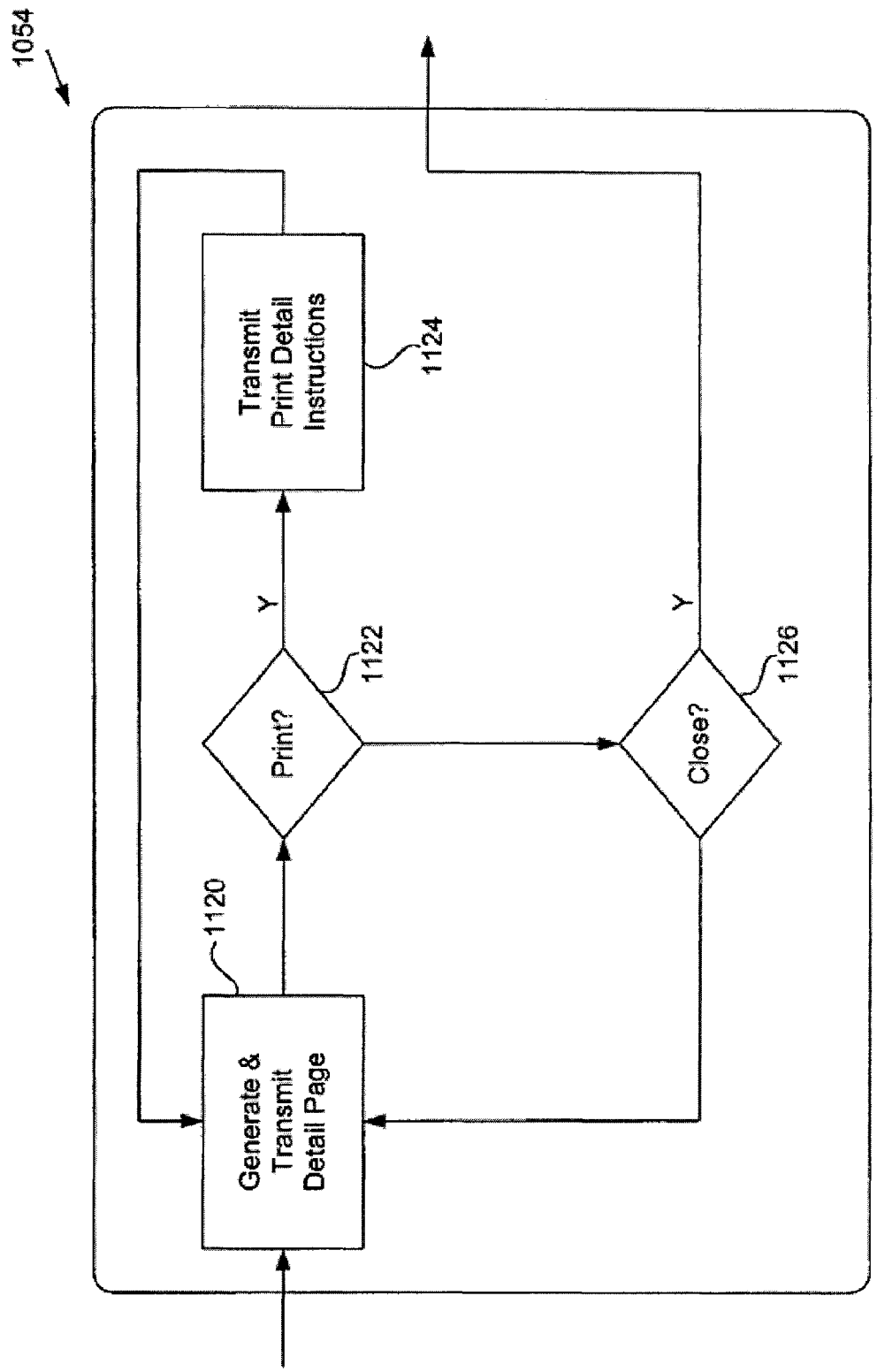

If it is determined that the client wishes to view a prescription detail page pertaining to a particular renewal request, (1052—Yes), a detail page process 1054 is followed, as shown in FIG. 10E. An example of a detail page is shown in FIG. 11 D. After the detail page process 1054 is completed, the active renewals page is regenerated and retransmitted, at 1040.

If it is determined that the client wishes to view the home page (1056—Yes), the active renewals page process 1020 exits and the home page is regenerated and retransmitted, at 1004 (FIG. 10A).

FIG. 10C is a flow chart of the archive page process 1022 of FIG. 10A. Only the aspects of the archive page process 1022 that differ from the active page process 1020 shown in FIG. 10B will be described.

In the archive page process 1022, at 1071, the Web-server procedures 830 (FIG. 8) generate and transmit an archived renewals page to the client computing device 801 (FIG. 8). The archived renewals page contains renewal request information, pertaining to the prescriber identified by the login username, regarding renewal requests which have already been reviewed by the prescriber. An example of an archived renewals page is shown in FIG. 11B.

If the Web-server procedures determine that the client wishes to implement an action button (1042—Yes), it is determined, at 1082, if the client wishes to implement an "update view" button. The "update view" button is used in conjunction with filter boxes where the client may input filter parameters such as the patient's name, the pharmaceutical identifier, approval date range, status of the renewal request, and the like. If it is determined that the client wishes to implement the "update view" button (1082—Yes), at 1084, the database management procedures 834 (FIG. 8) retrieve from the renewal database 850 (FIG. 8) data matching the filter parameters. The Web-server procedures 830 (FIG. 8) then generate and transmit, at 1071, an updated archived renewals page containing only renewal request information matching the filter parameters.

If it is determined that the client wishes to implement a "reset" button (1086—Yes), at 1088, the database management procedures 834 (FIG. 8) retrieve 1088 non-filtered data from the renewal database 850 (FIG. 8). The Web-server procedures 830 (FIG. 8) then generate and transmit, at 1071, an archived renewals page containing non-filtered renewal request information.

If the Web-server procedures determine that the client does not wish to implement an action button (1042—No) and determine that the client wishes to view the active renewals page (1072—Yes), an active renewals page process 1020 is followed, as shown in FIG. 10B.

FIG. 10D is a flow chart of the appointment page process 1024 of FIG. 10A. Only the aspects of the appointment page process 1024 that differ from the active page process 1020 shown in FIG. 10B will be described.

In the appointment page process 1024, at 1090, the Web-server procedures 830 (FIG. 8) generate and transmit to the client computing device 801 (FIG. 8) an appointment page pertaining to the prescriber identified by the login username. The appointment page contains information pertaining to patients with whom the prescriber wishes to make an appointment as indicated by the appointment indicator 858 (FIG. 9) in the renewal database 850 (FIG. 8). An example of an appointment page is shown in FIG. 11C.

If the Web-server procedures 830 (FIG. 8) determine that the client wishes to implement an action button (1042—Yes), it is determined, at 1096, if the client wishes to implement an "update list" button. The "update list" button is used in conjunction with check boxes where the client may select particular patients who have already made an appointment with the prescriber. If it is determined that the client wishes to implement the "update list" button (1096—Yes), the database management procedures 834 (FIG. 8) update, at 1098, the appointment made indicators 859 (FIG. 9) stored in the renewal database 850 (FIG. 8). The Web-server procedures 830 (FIG. 8) then generate and transmit, at 1090, an updated appointment page containing only patients with whom the prescriber wishes to make an appointment and who have not yet made an appointment.

If the Web-server procedures determine that the client does not wish to implement an action button (1042—No) and determine that the client wishes to view the active renewals page (1092—Yes), an active renewals page process 1020 is followed, as shown in FIG. 10B.

FIG. 10E is a flow chart of the detail page process 1054 of FIGS. 10B, 10C, and 10D. At 1120, the Web-server procedures 830 (FIG. 8) generate and transmit to the client computing device 801 (FIG. 8) a prescription detail page pertaining to a particular renewal request. The prescription detail page contains detailed information pertaining to a renewal request corresponding to a "prescription identifier" link which has been selected by the client from the active renewals page, archived renewals page, or the appointment page.

The Web-server procedures then determine, at 1122, whether the client wishes to print the current prescription detail page. If so, the Web-server procedures transmit, at 1124, instructions to the client computing device 801 (FIG. 8) to print the current prescription detail page.

If it is determined that the client does not wish to print the current prescription detail page (1122—No), it is then determined, at 1126, whether the client wishes to close the current prescription detail page. If so, the detail page process 1054 exits and the prior page (either the active renewals page, archived renewals page, or the appointment page) is regenerated and retransmitted (1040 of FIG. 10B, 1071 of FIG. 10C, or 1090 of FIG. 10D, respectively). If the client does not wish to close the current prescription detail page (1126—No), the process repeats and the prescription detail page is regenerated and retransmitted, at 1120.

FIG. 11A is a Graphical User Interface (GUI) of an active renewals page 1150. The active renewals page 1150 preferably contains information pertaining to renewal requests that have not been reviewed by the prescriber. The active renewals page 1150 also includes action buttons (1170, 1172, and 1174) and check boxes (1176) to allow the client to manage and control the information received and link buttons, such as an "active renewals" link button 1180, to view other pages. In addition, certain information, such as prescription identifier 1152, may be hyperlinked to other pages.

The information contained in the active renewals page 1150 preferably includes prescription identifier 1152 (corresponding to 862 of FIG. 9), patient information (corresponding to 856 of FIG. 9) such as patient name 1154 and patient date of birth 1156, a pharmaceutical identifier 1158 (corresponding to 864 of FIG. 9), renewal details for the prescribed pharmaceutical such as a renewal request date 1160 (corresponding to 882 of FIG. 9), and a print indicator 1162 (corresponding to 890 of FIG. 9) showing that a prescription detail page of a particular renewal request has been printed.

The action buttons include a "print list" button 1170 to print a list of all renewal requests contained on a current active renewals page, a "print selected" button 1172 to print a prescription detail page of all renewal requests selected by marking a check box 1176, and a "print all" button 1174 to print a prescription detail page of all renewal requests contained on a current active renewals page.

The hyperlinks include an "archived renewals" link button 1180 to view an archived renewals page, an "appointment tickler" link button 1182 to view an appointment page, a "home" link button 1184 to view the home page, and a "prescription identifier" link 1152, preferably a hyperlink, to view a prescription detail page corresponding to the prescription identifier. A hyperlink, as used herein, refers to a predefined linkage between one web page to another, displayed as text or as an icon.

FIG. 11B is a GUI of an archived renewals page 1200. The archived renewals page 1200 preferably includes information pertaining to renewal requests that have already been reviewed by the prescriber. The archived renewals page 1200 also includes action buttons (1220, 1222, 1224, 1230, and 1232) and check boxes (1226) to allow the client to manage and control the information received, and link buttons (1240, 1242, and 1244) and hyperlinked information 1202 to view other pages.

The information contained in the archived renewals page 1200 preferably includes a prescription identifier 1202 (corresponding to 862 of FIG. 9), patient information (corresponding to 856 of FIG. 9) such as patient name 1204 and patient date of birth 1206, a pharmaceutical identifier 1208 (corresponding to 864 of FIG. 9), renewal details for the prescribed pharmaceutical such as a renewal approval date 1210 (corresponding to 884 of FIG. 9) and a status indicator of the renewal request 1212 (corresponding to 886 of FIG. 9), and a print indicator 1214 (corresponding to 890 of FIG. 9) showing that a prescription detail page of a particular renewal request has been printed.

The action buttons include a "print list" button 1220 to print a list of all renewal requests contained on a current archived renewals page, a "print selected" button 1222 to print a prescription detail page of all renewal requests selected by a check box 1226, and a "print all" button 1224 to print a prescription detail page of all renewal requests contained on a current archived renewals page.

The action buttons also include an "update view" button 1230 to view an updated archived renewals page containing only archived renewal request information matching filter parameters received in filter boxes 1234. The filter boxes 1234 receive filter parameters such as the patient's name, the pharmaceutical identifier, an approval date range, status of the renewal request, and the like. The action buttons further includes a "reset" button 1232 to view an archived renewals page with non-filtered renewal request information.

The hyperlinks include an "active renewals" link button 1240 to view an active renewals page, an "appointment tickler" link button 1242 to view an appointment page, a "home" link button 1244 to view the home page, and a "prescription identifier" link 1202, preferably a hyperlink, to view a prescription detail page corresponding to the prescription identifier.

FIG. 11C is a GUI of an appointment page 1250. The appointment page 1250 preferably includes information pertaining to patients with whom the prescriber wishes to make an appointment. The appointment page 1250 also includes action buttons (1270, 1272, 1274, and 1280) and check boxes (1276 and 1282) to allow the client to control the information received and to update the renewal database 850 (FIG. 9) of the renewal server, and link buttons (1290, 1292, and 1294) and hyperlinked information 1252 to view other pages.

The information contained in the appointment page 1250 preferably includes a prescription identifier 1252 (corresponding to 862 of FIG. 9), patient information (corresponding to 856 of FIG. 9) such as patient name 1254, patient date of birth 1256, and patient contact details 1264, a pharmaceutical identifier 1258 (corresponding to 864 of FIG. 9), and renewal details for the prescribed pharmaceutical such as a renewal request approval date 1260 (corresponding to 884 of FIG. 9) and a status indicator of the renewal request 1262 (corresponding to 886 of FIG. 9).

The action buttons include a "print list" button 1270 to print a list of all renewal requests contained on a current appointment page, a "print selected" button 1272 to print a prescription detail page of all renewal requests selected by a check box 1276, and a "print all" button 1274 to print a prescription detail page of all renewal requests contained on a current appointment page. The action buttons also include an "update list" button 1280 to view an updated appointment page which excludes patients who have already made an appointment with the prescriber as indicated by a mark in an appointment check box 1282.

The hyperlinks include an "active renewals" link button 1290 to view an active renewals page, an "archived renewals" link button 1292 to view an archived renewals page, and a "home" link button 1294 to view the home page, and a "prescription identifier" link 1252, preferably a hyperlink, to view a prescription detail page corresponding to the prescription identifier.

FIG. 11D is a GUI of a prescription detail page 1300. This page is accessed by selecting a "prescription identifier" link 1152 (FIG. 11A), 1202 (FIG. 11B), or 1252 (FIG. 11C) in the active renewals page, archived renewals page, or appointment page. The prescription detail page 1300 preferably includes information pertaining to a renewal request associated with the prescription identifier corresponding to the "prescription identifier" link.

The information contained in the prescription detail page 1300 preferably includes patient information (corresponding to 856 of FIG. 9) such as patient name 1302, patient gender 1304, patient date of birth 1306, a dispenser identifier 1307 (corresponding to 863 of FIG. 9), a prescription identifier 1308 (corresponding to 862 of FIG. 9), a pharmaceutical identifier 1310 (corresponding to 864 of FIG. 9), dosage and refill details such as a dosage of the prescribed pharmaceutical 1312 (corresponding to 866 of FIG. 9), number of doses per refill 1314 (corresponding to 868 of FIG. 9), a number of refills 1316 (corresponding to 870 of FIG. 9) and a last refill date 1320 (corresponding to 872 of FIG. 9), renewal details for the prescribed pharmaceutical such as a renewal request date 1318 (corresponding to 882 of FIG. 9) and a renewal request approval date 1322 (corresponding to 884 of FIG. 9), and an appointment indicator 1324 (corresponding to 858 of FIG. 9) indicating whether the prescriber wishes to make an appointment with the patient.

The prescription detail page 1300 also preferably includes action buttons including a "print" button 1330 to print a current prescription detail page and a "close" button 1332 to close a current prescription detail page.

The foregoing description, for purposes of explanation, used specific nomenclature to provide a thorough understanding of the invention. Nevertheless, the foregoing descriptions of the preferred embodiments of the present invention are presented for purposes of illustration and description and are not intended to be exhaustive or to limit the invention to the precise forms disclosed; obvious modifications and variations are possible in view of the above teachings. Modern computer equipment and software facilitate numerous configurations of the various aspects of the present invention without deviating from the scope of the invention. For example, it does not matter whether the renewal server is part of or separate from the dispenser server. Furthermore, much of the data transfer can take place in either direction, while still accomplishing the desired end, e.g., transfer of information to a specific place. In addition, the various databases may be replaced by a central database. The renewal server, dispenser and prescriber then access the centralized database to obtain data. Access to the centralized database preferably occurs in real time via "always-on" connections. A skilled artisan will readily recognize that these and many other insubstantial variations of the preferred embodiments described above may be implemented without deviating from the scope of the present invention, as defined below.

What is claimed is:

1. A method for providing information regarding renewal requests for prescriptions, comprising:
   at a server system comprising one or more processors and memory:
      storing a plurality of renewal requests associated with a prescriber, each indicating that an existing prescription for a patient will expire unless the prescriber renews the prescription, and requesting that the prescriber renew the prescription, wherein the plurality of renewal requests include renewal requests for prescriptions of a plurality of patients;
      receiving a request for renewal requests associated with the prescriber from a client computer remote from the server;
      identifying, in a renewal database at least a subset of the renewal requests associated with the prescriber, wherein the subset includes at least two renewal requests associated with the prescriber;
      determining, by a processor, whether the prescriber has responded to the respective renewal requests in the subset;
      assigning a status to each of the renewal requests in the subset based on said determining;
      generating a report containing:
         representations of each of the renewal requests in the subset; and
         status indicators depicting the status of each of the renewal requests in the subset; and
      transmitting the report to the client computer, wherein the report includes representations of renewal requests from two or more different patients.

2. The method of claim 1, further comprising:
   receiving one or more filter parameters; and
   filtering the representations of renewal requests that are included in the report in accordance with the filter parameters.

3. The method of claim 2 wherein the filter parameters include one or more of: patient name, the pharmaceutical identifier, approval date range, or status of the renewal request.

4. The method of claim 1, further comprising:
   monitoring an expiration date of a respective prescription for a previously prescribed pharmaceutical by periodically determining whether a predetermined time period before the expiration date has been reached; and
   automatically generating a renewal request for the respective prescription before the expiration date for the respective prescription for the previously prescribed pharmaceutical has been reached.

5. The method of claim 1, wherein:
   the report includes print indicators for respective representations of renewal requests; and
   the print indicator for a respective representation of a respective renewal request indicates whether the respective renewal request has been printed by the prescriber.

6. The method of claim 1 wherein the report includes action buttons selected from a group consisting of: an update view button to view an updated page containing only information matching filter parameters received in filter boxes, a reset button to view a page containing non-filtered information, and an update list button to view a page which does not contain patients who have already made an appointment with the prescriber.

7. The method of claim 1 wherein:
   the report includes one or more prescription identifier links to view a prescription detail page; and
   the method further comprises, in response to detecting selection of a respective prescription identifier link button, displaying a prescription detail page that contains information regarding a renewal request associated with the respective prescription identifier corresponding to the respective prescription identifier link.

8. The method of claim 7, wherein the prescription detail page includes an appointment indicator enabling the prescriber to specify that the patient associated with the respective renewal request must make an appointment with the prescriber.

9. The method of claim 1 wherein:
   the report includes an active renewals link button to view an active renewals page; and
   the method further comprises, in response to detecting selection of the active renewals link button, displaying an active renewals page that contains information regarding renewal requests which have not yet been reviewed by the prescriber.

10. The method of claim 1 wherein:
    the report includes an archived renewals link button to view an archived renewals page; and
    the method further comprises, in response to detecting selection of the archived renewals link button, displaying an archived renewals page that contains information regarding renewal requests which have already been reviewed by the prescriber.

11. The method of claim 1 wherein:
    the report includes an appointment tickler link button to view an appointment page; and
    the method further comprises, in response to detecting selection of the appointment tickler link button, displaying an appointments page that contains information pertaining to patients with whom the prescriber has requested an appointment be scheduled.

12. A computer program product for use in conjunction with a computer system, the computer program product comprising a non-transitory computer readable storage medium and a computer program mechanism embedded therein, the computer program mechanism comprising instructions for:
   storing a plurality of renewal requests associated with a prescriber, each indicating that an existing prescription for a patient will expire unless the prescriber renews the prescription, and requesting that the prescriber renew the prescription, wherein the plurality of renewal requests include renewal requests for prescriptions of a plurality of patients;
   receiving a request for renewal requests associated with the prescriber from a client computer remote from the server;
   identifying, in a renewal database at least a subset of the renewal requests associated with the prescriber, wherein the subset includes at least two renewal requests associated with the prescriber;
   determining, by a processor, whether the prescriber has responded to the respective renewal requests in the subset;
   assigning a status to each of the renewal requests in the subset based on said determining;
   generating a report containing:
      representations of each of the renewal requests in the subset; and
      status indicators depicting the status of each of the renewal requests in the subset; and
   transmitting the report to the client computer, wherein the report includes representations of renewal requests from two or more different patients.

13. The computer program product of claim 12, further comprising instructions for:
   receiving one or more filter parameters; and
   filtering the representations of renewal requests that are included in the report in accordance with the filter parameters.

14. The computer program product of claim 13, wherein the filter parameters include one or more of: patient name, the pharmaceutical identifier, approval date range, or status of the renewal request.

15. The computer program product of claim 12, further comprising instructions for:
   monitoring an expiration date of a respective prescription for a previously prescribed pharmaceutical by periodically determining whether a predetermined time period before the expiration date has been reached; and
   automatically generating a renewal request for the respective prescription before the expiration date for the respective prescription for the previously prescribed pharmaceutical has been reached.

16. The computer program product of claim 12, wherein:
   the report includes print indicators for respective representations of renewal requests; and
   the print indicator for a respective representation of a respective renewal request indicates whether the respective renewal request has been printed by the prescriber.

17. The computer program product of claim 12, wherein the report includes action buttons selected from a group consisting of: an update view button to view an updated page containing only information matching filter parameters received in filter boxes, a reset button to view a page containing non-filtered information, and an update list button to view a page which does not contain patients who have already made an appointment with the prescriber.

18. The computer program product of claim 12, wherein:
   the report includes one or more prescription identifier links to view a prescription detail page; and
   the computer program product further comprises instructions for, in response to detecting selection of a respective prescription identifier link button, displaying a prescription detail page that contains information regarding a renewal request associated with the respective prescription identifier corresponding to the respective prescription identifier link.

19. The computer program product of claim 18, wherein the prescription detail page includes an appointment indicator enabling the prescriber to specify that the patient associated with the respective renewal request must make an appointment with the prescriber.

20. The computer program product of claim 12, wherein:
   the report includes an active renewals link button to view an active renewals page; and
   the computer program product further comprises instructions for, in response to detecting selection of the active renewals link button, displaying an active renewals page that contains information regarding renewal requests which have not yet been reviewed by the prescriber.

21. The computer program product of claim 12, wherein:
   the report includes an archived renewals link button to view an archived renewals page; and
   the computer program product further comprises instructions for, in response to detecting selection of the archived renewals link button, displaying an archived renewals page that contains information regarding renewal requests which have already been reviewed by the prescriber.

22. The computer program product of claim 12, wherein:
   the report includes an appointment tickler link button to view an appointment page; and
   the computer program product further comprises instructions for, in response to detecting selection of the appointment tickler link button, displaying an appointments page that contains information pertaining to patients with whom the prescriber has requested an appointment be scheduled.

23. A computer system, comprising:
   at least one processor;
   memory; and
   one or more procedures wherein the one or more procedures are stored in the memory and configured to be executed by the at least one processor, the one or more procedures including instructions for:
      storing a plurality of renewal requests associated with a prescriber, each indicating that an existing prescription for a patient will expire unless the prescriber renews the prescription, and requesting that the prescriber renew the prescription, wherein the plurality of renewal requests include renewal requests for prescriptions of a plurality of patients;
      receiving a request for renewal requests associated with the prescriber from a client computer remote from the server;
      identifying, in a renewal database at least a subset of the renewal requests associated with the prescriber, wherein the subset includes at least two renewal requests associated with the prescriber;
      determining, by a processor, whether the prescriber has responded to the respective renewal requests in the subset;

assigning a status to each of the renewal requests in the subset based on said determining;

generating a report containing:
representations of each of the renewal requests in the subset; and
status indicators depicting the status of each of the renewal requests in the subset; and
transmitting the report to the client computer, wherein the report includes representations of renewal requests from two or more different patients.

24. The system of claim 23, further comprising instructions for:
receiving one or more filter parameters; and
filtering the representations of renewal requests that are included in the report in accordance with the filter parameters.

25. The system of claim 24, wherein the filter parameters include one or more of: patient name, the pharmaceutical identifier, approval date range, or status of the renewal request.

26. The system of claim 13, further comprising instructions for:
monitoring an expiration date of a respective prescription for a previously prescribed pharmaceutical by periodically determining whether a predetermined time period before the expiration date has been reached; and
automatically generating a renewal request for the respective prescription before the expiration date for the respective prescription for the previously prescribed pharmaceutical has been reached.

27. The system of claim 23, wherein:
the report includes print indicators for respective representations of renewal requests; and
the print indicator for a respective representation of a respective renewal request indicates whether the respective renewal request has been printed by the prescriber.

28. The system of claim 23, wherein the report includes action buttons selected from a group consisting of: an update view button to view an updated page containing only information matching filter parameters received in filter boxes, a reset button to view a page containing non-filtered information, and an update list button to view a page which does not contain patients who have already made an appointment with the prescriber.

29. The system of claim 23, wherein:
the report includes one or more prescription identifier links to view a prescription detail page; and
the system further comprises instructions for, in response to detecting selection of a respective prescription identifier link button, displaying a prescription detail page that contains information regarding a renewal request associated with the respective prescription identifier corresponding to the respective prescription identifier link.

30. The system of claim 29, wherein the prescription detail page includes an appointment indicator enabling the prescriber to specify that the patient associated with the respective renewal request must make an appointment with the prescriber.

31. The system of claim 23, wherein:
the report includes an active renewals link button to view an active renewals page; and
the system further comprises instructions for, in response to detecting selection of the active renewals link button, displaying an active renewals page that contains information regarding renewal requests which have not yet been reviewed by the prescriber.

32. The system of claim 23, wherein:
the report includes an archived renewals link button to view an archived renewals page; and
the system further comprises instructions for, in response to detecting selection of the archived renewals link button, displaying an archived renewals page that contains information regarding renewal requests which have already been reviewed by the prescriber.

33. The system of claim 23, wherein:
the report includes an appointment tickler link button to view an appointment page; and
the system further comprises instructions for, in response to detecting selection of the appointment tickler link button, displaying an appointments page that contains information pertaining to patients with whom the prescriber has requested an appointment be scheduled.

* * * * *